US011458413B2

(12) United States Patent
Crawford et al.

(10) Patent No.: US 11,458,413 B2
(45) Date of Patent: Oct. 4, 2022

(54) ENERGY-EFFICIENT SYSTEMS INCLUDING VAPOR COMPRESSION FOR BIOFUEL OR BIOCHEMICAL PLANTS

(71) Applicant: Energy Integration, Inc., Boulder, CO (US)

(72) Inventors: Lynn Allen Crawford, Aurora, CO (US); William Bryan Schafer, III, Boulder, CO (US)

(73) Assignee: Energy Integration, Inc., Boulder, CO (US)

( * ) Notice: Subject to any disclaimer, the term of this patent is extended or adjusted under 35 U.S.C. 154(b) by 614 days.

(21) Appl. No.: 15/711,699

(22) Filed: Sep. 21, 2017

(65) Prior Publication Data

US 2018/0028934 A1 Feb. 1, 2018

Related U.S. Application Data

(63) Continuation-in-part of application No. 15/453,881, filed on Mar. 8, 2017, now Pat. No. 9,925,476.
(Continued)

(51) Int. Cl.
*B01D 1/28* (2006.01)
*B01D 3/32* (2006.01)
(Continued)

(52) U.S. Cl.
CPC ......... *B01D 1/2856* (2013.01); *B01D 1/2843* (2013.01); *B01D 1/2887* (2013.01);
(Continued)

(58) Field of Classification Search
USPC ........................................................ 203/26
See application file for complete search history.

(56) References Cited

U.S. PATENT DOCUMENTS 4,340,446 A * 7/1982 Crawford ............. B01D 1/2806
203/19
4,422,903 A 12/1983 Messick et al.
(Continued)

FOREIGN PATENT DOCUMENTS

WO WO-2019059915 A1 * 3/2019 ............. C10G 47/00

OTHER PUBLICATIONS

WO2019059915_ISR_WOISA, WO-2019059915-A1 Abstract, Int'l Search Report (ISR), Written Opinion Int'l Search Authority (WOISA), dated Dec. 5, 2017, 10 pages. (Year: 2017).*

*Primary Examiner* — Hayden Brewster
(74) *Attorney, Agent, or Firm* — O'Connor & Company; Ryan P. O'Connor

(57) ABSTRACT

Processes and systems are provided to compress vapors produced in distillation and recover the heat of condensation through vapor compression and to derive mechanical, thermal, and electrical energy from a combined heat and power system, while maintaining the plant's original ability to operate. The plant's existing distillation system, steam generation, and electrical demand determine the design basis for the retrofit system that is targeted at an optimized combination of energy usage, energy cost, and environmental impact. Vapor compression (by mechanical vapor recompression and/or thermal vapor recompression) minimizes the total energy usage. Optionally, combined heat and power provides a means of converting energy between fuel, electricity, and thermal energy in a manner that best complements plant requirements and energy economics and minimizes inefficiencies and energy losses.

22 Claims, 10 Drawing Sheets

Related U.S. Application Data

(60) Provisional application No. 62/414,165, filed on Oct. 28, 2016, provisional application No. 62/330,847, filed on May 3, 2016, provisional application No. 62/314,358, filed on Mar. 28, 2016.

(51) Int. Cl.
  *B01D 3/00* (2006.01)
  *B01D 3/14* (2006.01)
  *C12P 7/40* (2006.01)

(52) U.S. Cl.
  CPC ............ *B01D 3/001* (2013.01); *B01D 3/002* (2013.01); *B01D 3/007* (2013.01); *B01D 3/14* (2013.01); *B01D 3/322* (2013.01); *C12P 7/40* (2013.01); *Y02P 70/10* (2015.11)

(56) References Cited

U.S. PATENT DOCUMENTS

| | | |
|---|---|---|
| 4,536,258 A | 8/1985 | Huhta-Koivisto |
| 4,539,076 A * | 9/1985 | Swain ............... B01D 1/2856 202/154 |
| 4,585,523 A | 4/1986 | Giddings |
| 4,645,569 A | 2/1987 | Akabane et al. |
| 4,692,218 A | 9/1987 | Houben et al. |
| 4,746,610 A | 5/1988 | Smith |
| 5,294,304 A | 3/1994 | Kano et al. |
| 5,586,442 A * | 12/1996 | Nicodemus ............... F04F 5/00 62/107 |
| 5,772,850 A | 6/1998 | Morris |
| 7,257,945 B2 | 8/2007 | Kass et al. |
| 8,101,217 B2 | 1/2012 | Sovereign et al. |
| 8,101,808 B2 | 1/2012 | Evanko et al. |
| 8,114,255 B2 | 2/2012 | Vane et al. |
| 8,128,787 B2 | 3/2012 | Wynn et al. |
| 8,283,505 B2 | 10/2012 | Evanko et al. |
| 8,304,588 B2 | 11/2012 | Evanko et al. |
| 8,614,077 B2 | 2/2013 | Evanko et al. |
| 8,535,413 B2 | 11/2013 | Bryan et al. |
| 9,138,678 B2 | 9/2015 | Huang et al. |
| 9,925,476 B2 * | 3/2018 | Crawford ................. B01D 3/14 |
| 9,925,477 B2 * | 3/2018 | Crawford ............. B01D 1/2843 |
| 2014/0013783 A1 * | 1/2014 | Xiang .................. B01D 1/0041 62/122 |
| 2014/0311889 A1 * | 10/2014 | Zaher ..................... B01D 3/002 203/42 |
| 2014/0322777 A1 * | 10/2014 | Clark ........................ C12P 7/18 435/158 |
| 2016/0002131 A1 * | 1/2016 | Glasspool ................ B01D 1/28 203/18 |
| 2017/0274297 A1 * | 9/2017 | Crawford ............... B01D 3/065 |

* cited by examiner

ENERGY-EFFICIENT SYSTEMS INCLUDING VAPOR COMPRESSION FOR BIOFUEL OR BIOCHEMICAL PLANTS

PRIORITY DATA

This patent application is a continuation-in-part application of U.S. patent application Ser. No. 15/453,881, filed on Mar. 8, 2017, which is a non-provisional application claiming priority to U.S. Provisional Patent App. No. 62/314,358, filed on Mar. 28, 2016; U.S. Provisional Patent App. No. 62/330,847, filed on May 3, 2016; and U.S. Provisional Patent App. No. 62/414,165, filed on Oct. 28, 2016, each of which is hereby incorporated by reference herein.

FIELD OF THE INVENTION

The present invention generally relates to processes, systems, and apparatus for recovery and refinement of bio-products from bio-fermentation plants requiring distillation.

BACKGROUND OF THE INVENTION

The process energy consumed in the distillation of bio-products often constitutes the largest energy requirement in the production life cycle of those products. Distillation systems are designed to meet a number of requirements appropriate to the priorities existing when design and investment decisions are made. First-generation distillation systems were implemented when simplicity was highly prized and environmental concerns related to energy usage were largely relegated to minimizing associated hazardous emissions. Today, policies and regulatory initiatives targeting the reduction of greenhouse gas emissions are impacting consumers and producers of energy, creating incentives for improving energy efficiency and minimizing environmental footprints.

Examples of regulation impacting energy consumers and producers include California's Low Carbon Fuel Standard (LCFS) and the U.S. EPA's Clean Power Plan. The LCFS models life cycle fuel pathways to assign a Carbon Intensity (CI) to fuels that reflects a fuel's carbon dioxide emissions. A fuel producer's pathway, reflecting the CI for their process, generates credits or requires the purchase of credits from other producers to meet California's CI targets. These credits are traded on an exchange that establishes their value and permits monetization by producers. Improvements in process energy efficiency are directly rewarded through the LCFS system, incentivizing energy efficiency investments. This system, and similar systems under consideration by governmental authorities, directly reward producers for reducing their energy requirements, even when low energy prices provide little or no incentive to make such investments.

Bio-fermentation products, which include biofuels, are the result of the investment of energy by growing a biological raw material which is then converted by chemical processing to a purified liquid fuel, with each step requiring energy-intensive stages which include distillation. Conventional, first-generation methods employed at a bio-distillery plant expend significant energy in distillation (including distillation, evaporations, and possibly dehydrations) and drying. The inefficiency of these methods negatively impacts producer economics as well as the environmental footprint ascribed to the process.

Improvements in overall energy efficiency and optimization are still needed commercially for new or existing distilleries, or new or existing biorefineries employing distillation.

SUMMARY OF THE INVENTION

Some variations of the invention provide an energy-efficient system configured for a distillery or biorefinery, wherein the distillery or biorefinery is capable of converting biomass into a biofuel or biochemical, and wherein the distillery or biorefinery includes a distillation unit configured for distillation to purify the biofuel or biochemical, the system comprising:
  (i) a vapor compression sub-system comprising a mechanical vapor recompression (MVR) unit and/or a thermal vapor recompression (TVR) unit, wherein the vapor compression sub-system is configured to recover latent heat and provide a reduction in process thermal energy usage in the distillery or biorefinery; and
  (ii) an an optional combined heat and power (CHP) sub-system having a CHP engine, configured to provide mechanical, electrical, and/or thermal energy for driving the vapor compression sub-system, wherein when the CHP sub-system is present, the CHP sub-system and the vapor compression sub-system are integrated and configured so that residual waste heat of the CHP engine offsets process thermal energy usage in the distillery or biorefinery.

In some embodiments, the vapor compression sub-system comprises multiple mechanical and/or thermal compressors or vapor jets, wherein cascaded heat to or from the distillation unit is integrated with multiple stillage evaporations and/or dehydration, and wherein compressed biofuel or biochemical vapors and generated steam are returned to the distillation unit within the system.

In some embodiments, the vapor compression sub-system comprises multiple mechanical and/or thermal compressors or vapor jets, wherein cascaded heat to or from the distillation unit is integrated with multiple stillage evaporations including a first or last multiple evaporator, wherein compressed steam from the first evaporator is optionally split between the distillation unit and a part of the multiple stillage evaporations, and wherein a compressor stage is configured to cascade latent heat between the distillation unit and the multiple stillage evaporations.

In some embodiments, the vapor compression sub-system comprises multiple mechanical and/or thermal compressors or vapor jets, wherein cascaded heat to or from multiple stillage evaporations to the distillation unit is integrated with compression of steam to or from at least one reboiler-evaporator to drive the distillation and partial evaporation, and/or wherein compressor stages are configured to cascade the latent heat from the distillation process unit into an evaporation unit.

In some embodiments, the vapor compression sub-system comprises multiple mechanical and/or thermal compressors or vapor jets, wherein cascaded latent heat from the distillation process unit is integrated to drive vapor-phase dehydration of a vapor stream output of the distillation unit.

In certain embodiments, the energy-efficient system comprises a dryer configured for drying stillage derived from the distillation unit, wherein the vapor compression sub-system comprises both an MVR unit configured to recover the latent heat of the distillation and a TVR unit configured to recover latent heat from exhaust gases from the dryer.

In these or other embodiments, the energy-efficient system comprises a dryer configured for drying stillage derived from the distillation unit, wherein the vapor compression sub-system comprises multiple mechanical and/or thermal compressors or vapor jets, and wherein cascaded latent heat from an exhaust of the dryer, recaptured by a reboiler-evaporator, is integrated to provide steam for other plant processes.

The CHP sub-system is present within the energy-efficient system, in some variations of the invention. When the CHP sub-system is present, the CHP engine may be sized in concert with energy demand of the vapor compression sub-system and/or thermal energy demand of the distillery or biorefinery, wherein waste heat recovered by the CHP sub-system provides at least some of the thermal energy demand of the distillery or biorefinery.

In these or other embodiments in which the CHP sub-system is present, the vapor compression sub-system comprises a TVR unit, wherein the CHP engine is sized in concert with motive vapor demand of the TVR unit.

Other variations of the invention provide a method of modifying a distillery or biorefinery, wherein the distillery or biorefinery converts biomass into a biofuel or biochemical, and wherein the biofuel or biochemical is purified by distillation, the method comprising:
  (i) introducing a vapor compression unit comprising a mechanical vapor recompression (MVR) unit and/or a thermal vapor recompression (TVR) unit to recover latent heat and provide a reduction in process thermal energy usage in the distillery or biorefinery; and
  (ii) optionally introducing a combined heat and power (CHP) system having a CHP engine, to provide mechanical, electrical, and/or thermal energy for driving the vapor compression unit, wherein when the CHP system is present, (a) residual waste heat of the CHP engine offsets process thermal energy usage in the distillery or biorefinery, in conjunction with the vapor compression unit, and (b) integration of the vapor compression unit with the CHP system is balanced to optimize process energy requirements, process carbon intensity, and/or process energy costs.

In some embodiments, the vapor compression unit comprises multiple mechanical and/or thermal vapor compressors or vapor jets, wherein cascaded latent heat from the distillation is integrated with multiple stillage evaporations and/or dehydration, and wherein compressed biofuel or biochemical vapors and generated steam are returned to the distillation.

In some embodiments, the vapor compression unit comprises multiple mechanical and/or thermal vapor compressors or vapor jets, wherein cascaded latent heat from the distillation is integrated with multiple stillage evaporations including a first evaporator, wherein compressed steam from the first evaporator is optionally split between the distillation and a part of the multiple stillage evaporations, and wherein the distillation and at least a portion of the multiple stillage evaporations are operated at equal or near-equal pressure, thereby allowing a compressor stage to cascade the latent heat of evaporation between the distillation and the multiple stillage evaporations and optionally vapor-phase dehydration.

In some embodiments, the vapor compression unit comprises multiple mechanical and/or thermal vapor compressors or vapor jets, wherein cascaded latent heat from multiple stillage evaporations to the distillation is integrated with compression of steam from at least one reboiler-evaporator to drive the distillation and partial evaporation, and wherein the distillation and the partial evaporation are operated such that evaporation pressure is higher than distillation pressure, thereby allowing compressor stages to cascade the latent heat of evaporation into the distillation. Optionally, compression of the distillation vapors is integrated with dehydration of distillation vapors at a sufficient pressure to generate a final product containing the biofuel or biochemical.

In some embodiments, the vapor compression unit is sized or operated with a standard steam generator for reduction of thermal energy required in the distillation, evaporation, and/or dehydration, wherein the standard steam generator is operated at a reduced rate as a result of reduction in steam energy demand due to energy recovered by the vapor compression unit.

When the CHP system is present, the CHP engine may be sized or operated in concert with energy demand of the vapor compression unit and thermal energy demand of the distillery or biorefinery, wherein at least some of the thermal energy demand of the distillery or biorefinery is provided by waste heat recovered by the CHP system.

In certain embodiments in which the CHP system is present, the vapor compression unit comprises a TVR unit, and the CHP engine is sized or operated in concert with thermal energy demand for producing steam or biochemical motive vapors to drive the TVR unit.

Integration of the vapor compression unit with the optional CHP system allows balancing of use in the distillery or biorefinery of process fuel energy, electrical energy unit price, and process carbon intensity, wherein the process energy costs are minimized based on relative market pricing of the process fuel energy and the electrical energy, and optionally wherein total process energy is not minimized.

In various embodiments, the biofuel or biochemical is selected from the group consisting of methanol, ethanol, 1-propanol, 2-propanol, n-butanol, isobutanol, 2-butanol, tert-butanol, acetone, and combinations thereof.

BRIEF DESCRIPTION OF THE FIGURES

Each of FIG. 1, FIG. 2, FIG. 3, FIG. 4, FIG. 5, FIG. 6, FIG. 7, FIG. 8, FIG. 9.

Power used in driving vapor compression may be provided by combined heat and power (CHP) or any other source of power including, but not limited to, the utility grid, solar arrays, wind turbines, or other forms of power generation. Each of FIGS. 1 to 10 should be understood to represent this optionality of CHP. That is, while the drawings include CHP as being present, in alternative embodiments the CHP is replaced by (or augmented with) any other source of heat and/or power.

In FIGS. 1 to 10, Section I encompasses a distillery flow diagram, and Section II encompasses the added vapor compression (MVR and/or TVR) and the optional CHP of variations of the invention. The schema splits Section I and Section II at the distillation tower, with standard steam-driven distillation on the left side of the tower in Section I and on the right side of the tower mechanical vapor compression with the optional combined heat and power (MVR/TVR-CHP) in Section II. Section III is split from Sections I and II at the dryer drum having MVR/TVR heat recovery from the exhaust gases.

Figure 1:
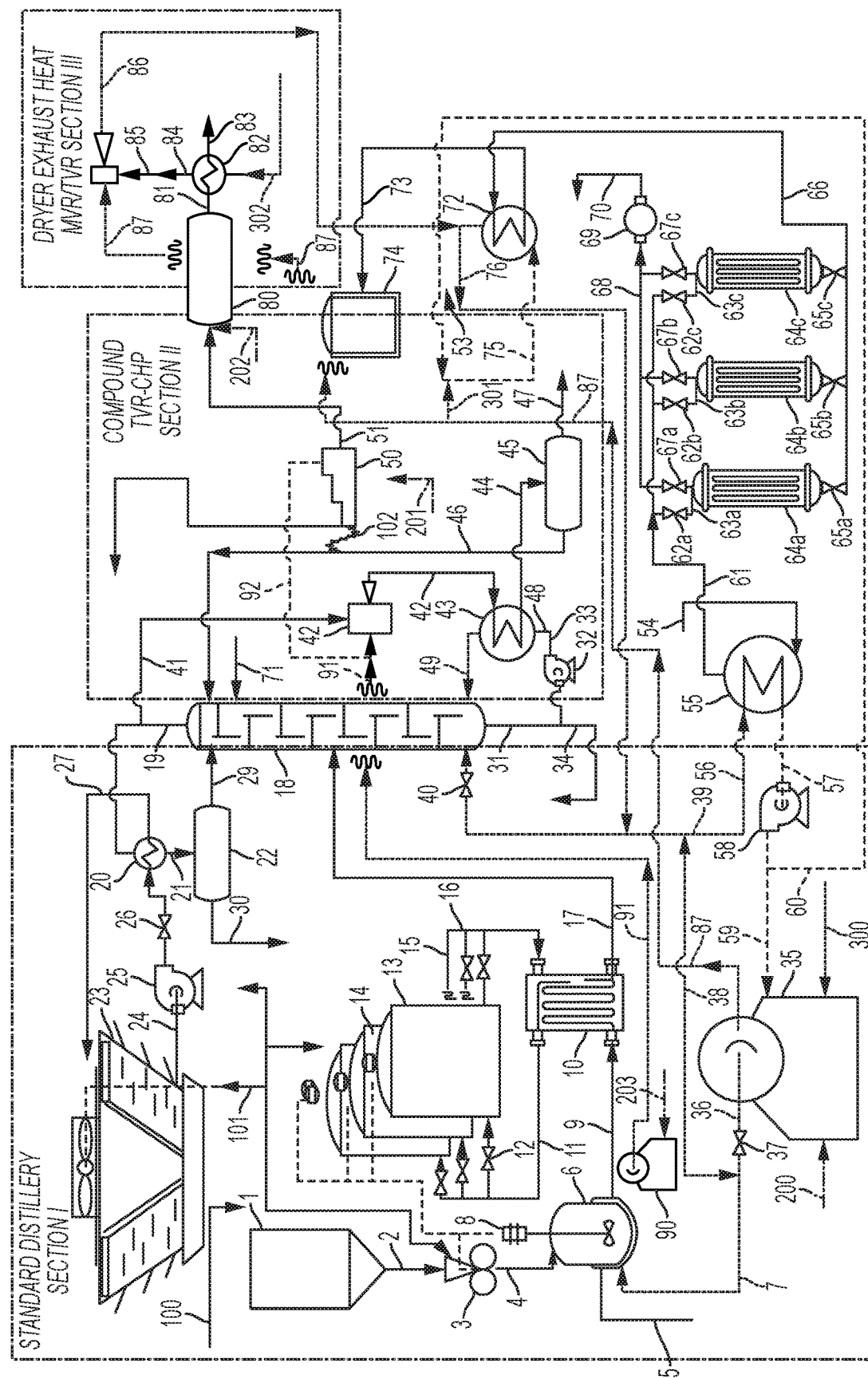

FIG. 1 is a schematic drawing in which Section II depicts a process wherein the waste heat from the optional CHP is used to generate process steam through Heat Recovery for Steam Generation (HRSG), with the generated steam being used to meet steam demands of the distillery.

Figure 2:
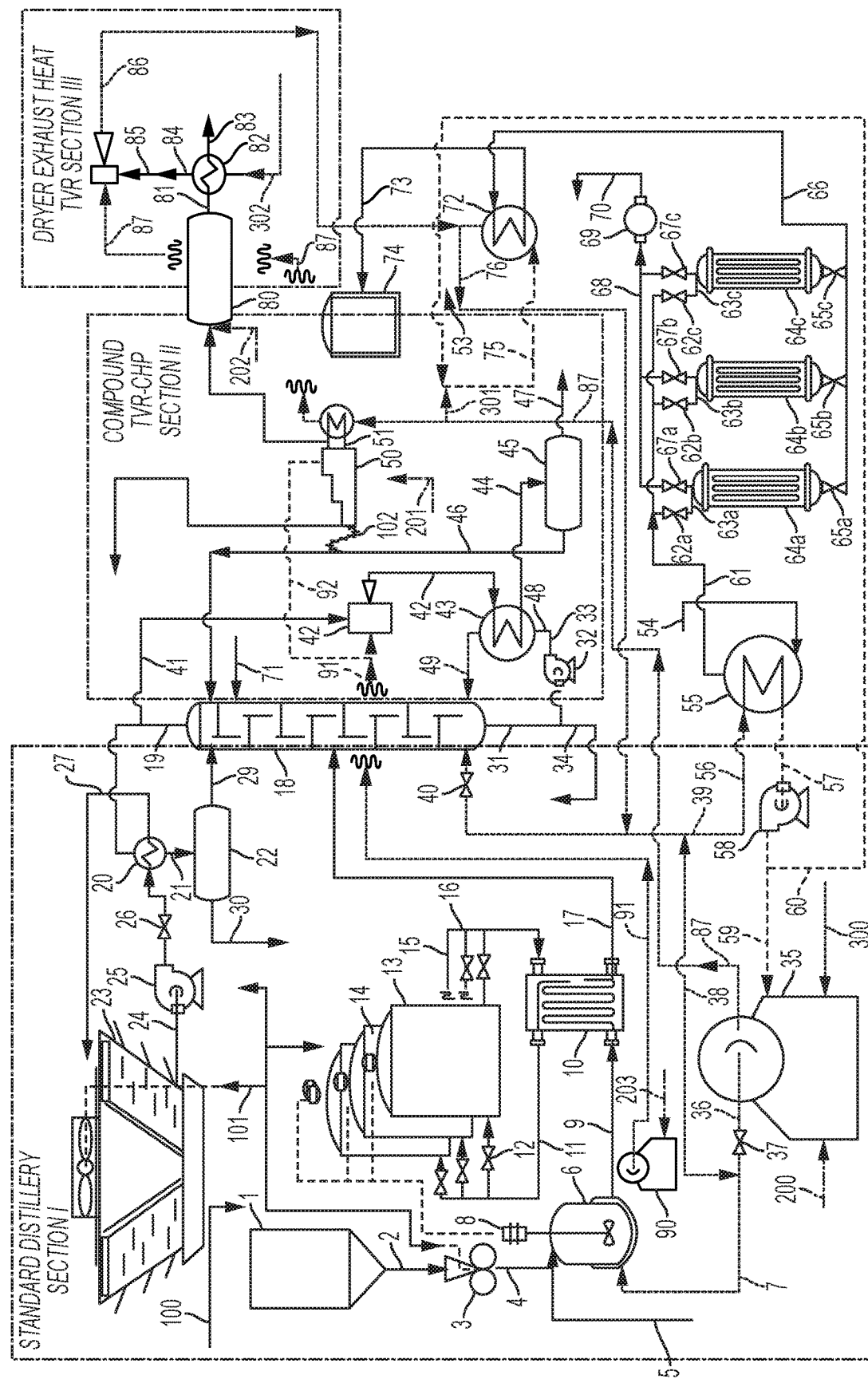

FIG. 2 is a schematic drawing in which Section II depicts a process in which the waste heat from the optional CHP is used to generate process steam through Heat Recovery for Steam Generation (HRSG), with the generated steam being used to meet the steam demand of the distillery and with a portion of the optional CHP waste heat being used to directly dry the distillery co-products.

Figure 3:
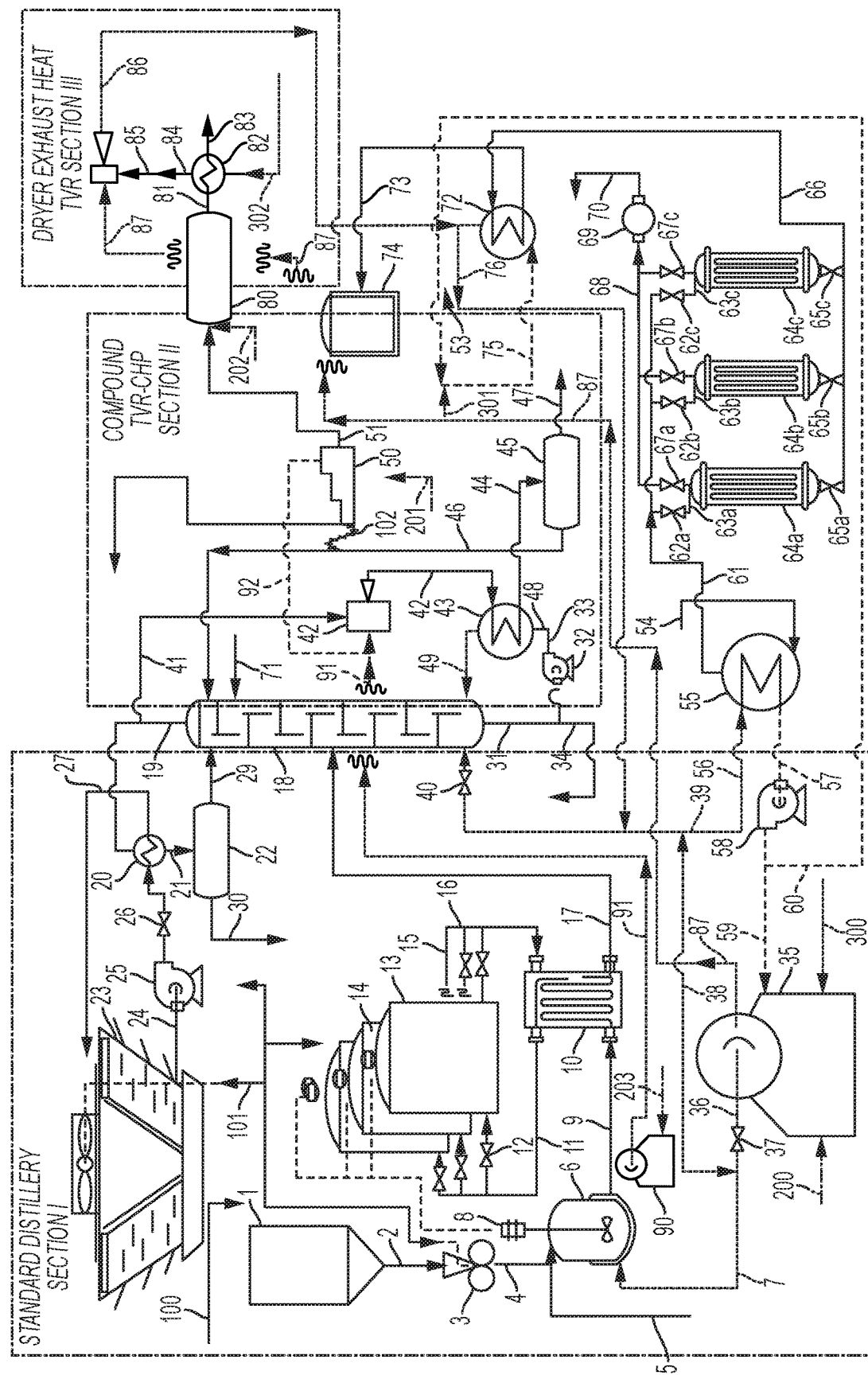

FIG. 3 is a schematic drawing in which Section II depicts a process in which the waste heat from the optional CHP is exclusively used to directly dry the distillery co-products.

Figure 4:
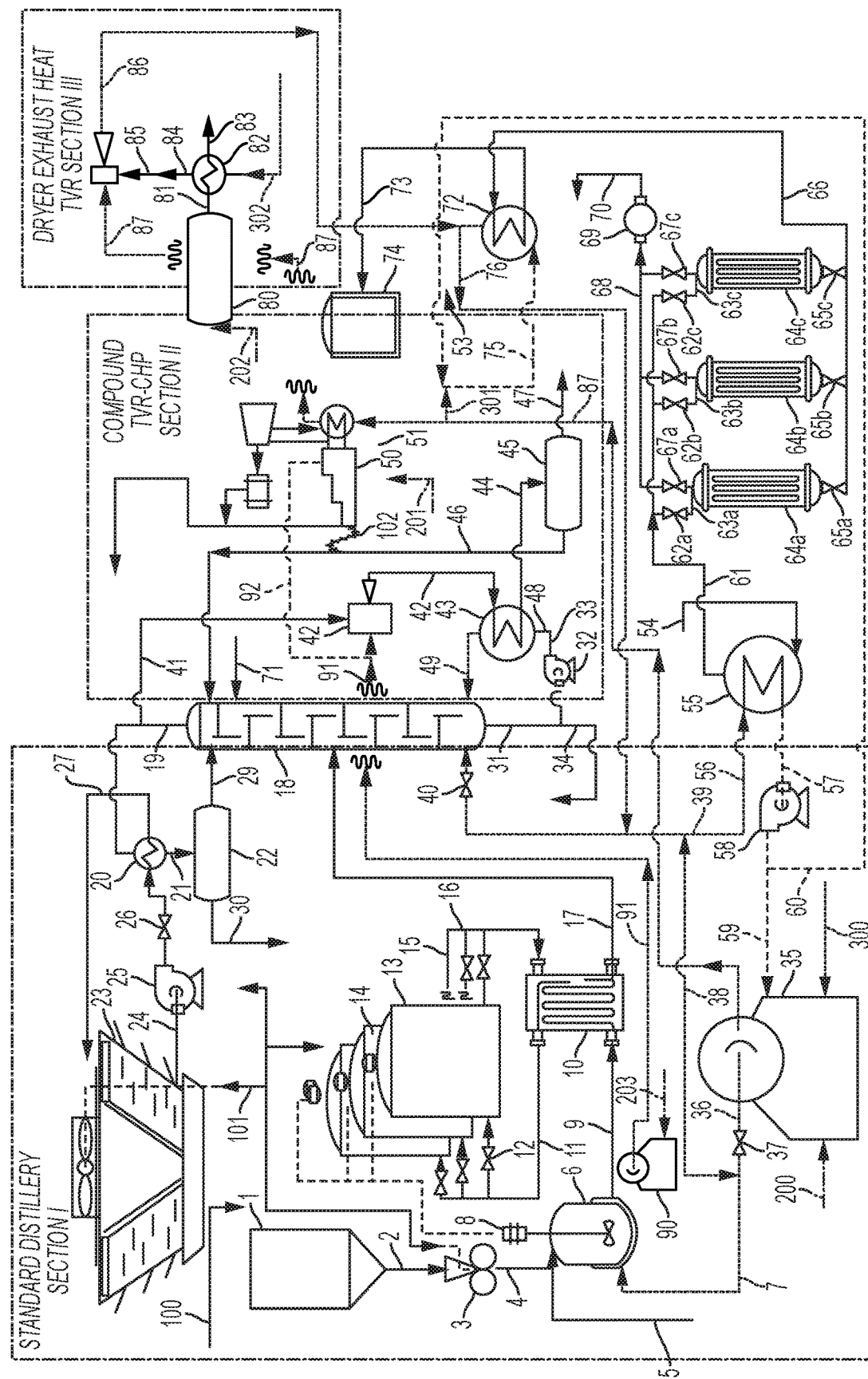

FIG. 4 is a schematic drawing in which Section II depicts a process in which the waste heat from the optional CHP is used to generate process steam by Heat Recovery for Steam Generation (HRSG), with the generated steam used to generate additional electrical power in a steam turbine to meet further electrical demand of the distillery or to sell onto the power grid. The low-pressure steam exiting the optional co-generation turbine is used as process steam to meet the process steam demand of the distillery.

Figure 5:
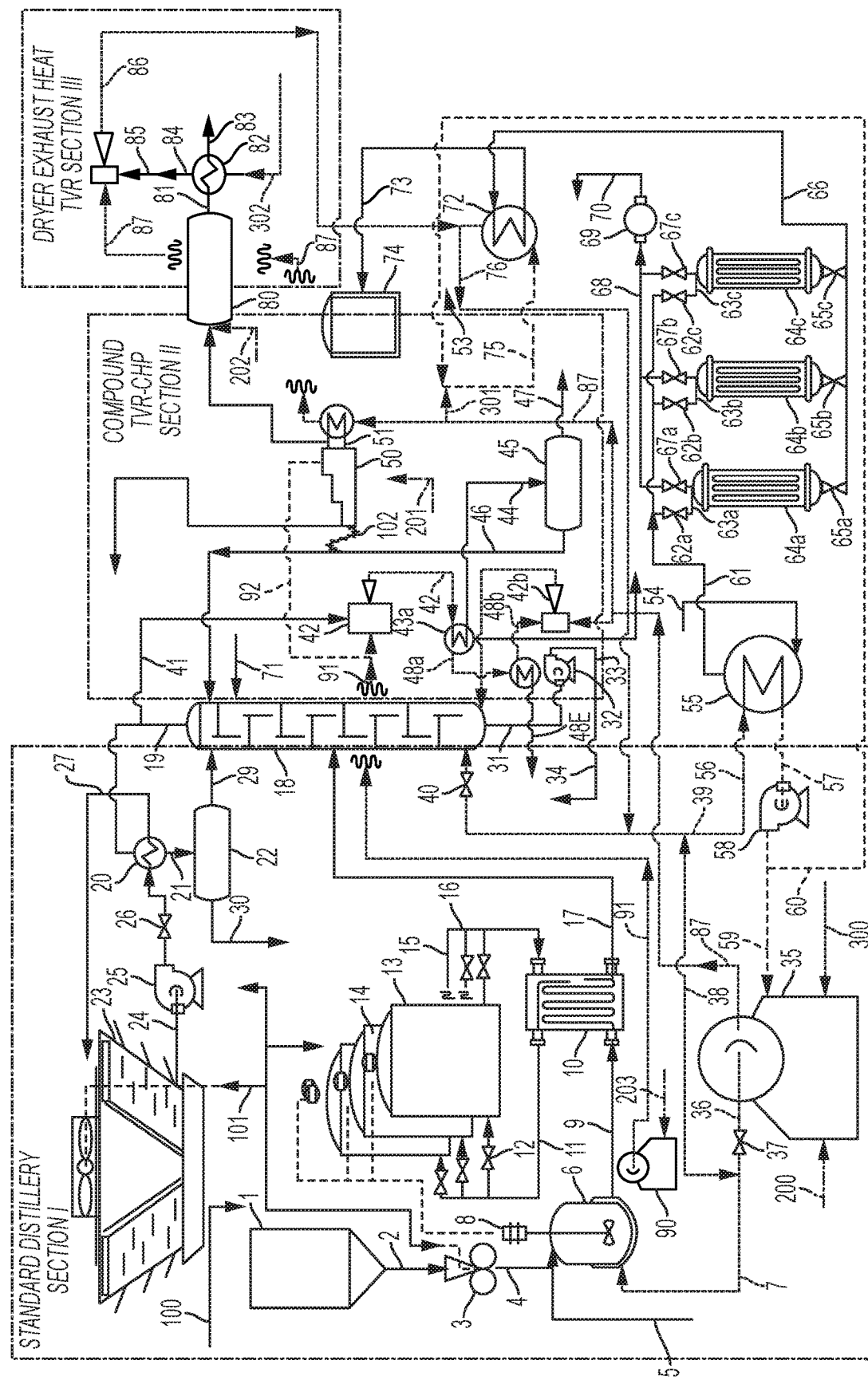

FIG. 5 is a schematic drawing in which Section II depicts a process in which the distillation vapors are passed to a multi-effect evaporation process with the steam from the final effect compressed and passed to the distillation. This integration of vapor compression with evaporation together with the optional CHP is implied for the process configurations described in FIGS. 1, 2, 3, and 4.

Figure 6:
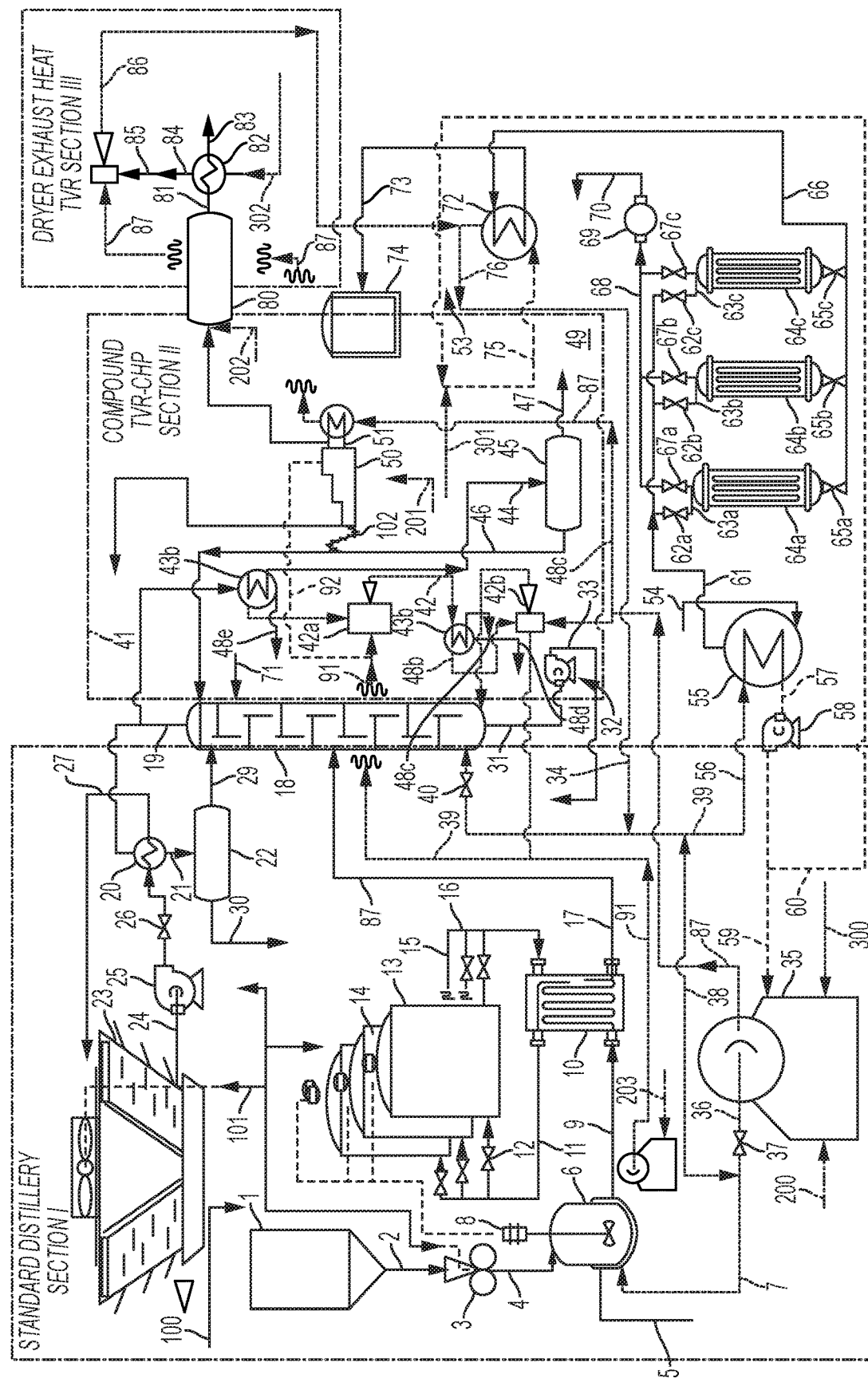

FIG. 6 is a schematic drawing in which Section II depicts a process by which distillation vapors are passed to a multi-effect evaporation process with the biofuel or biochemical vapors condensing in the first effect. The produced steam passes to multiple compressor stages, with the first compressor stage intake passing from the lowest-pressure effect evaporator, passing steam on to another effect where it is compressed and passes to the later evaporators and the distillation process. In the distillation process, the pressure of the distillation and the high-pressure evaporation effect are preferably operated at a common pressure, allowing one common compressor. This integration of vapor compression with evaporation is implied for the process configurations described in FIGS. 1, 2, 3, and 4.

Figure 7:
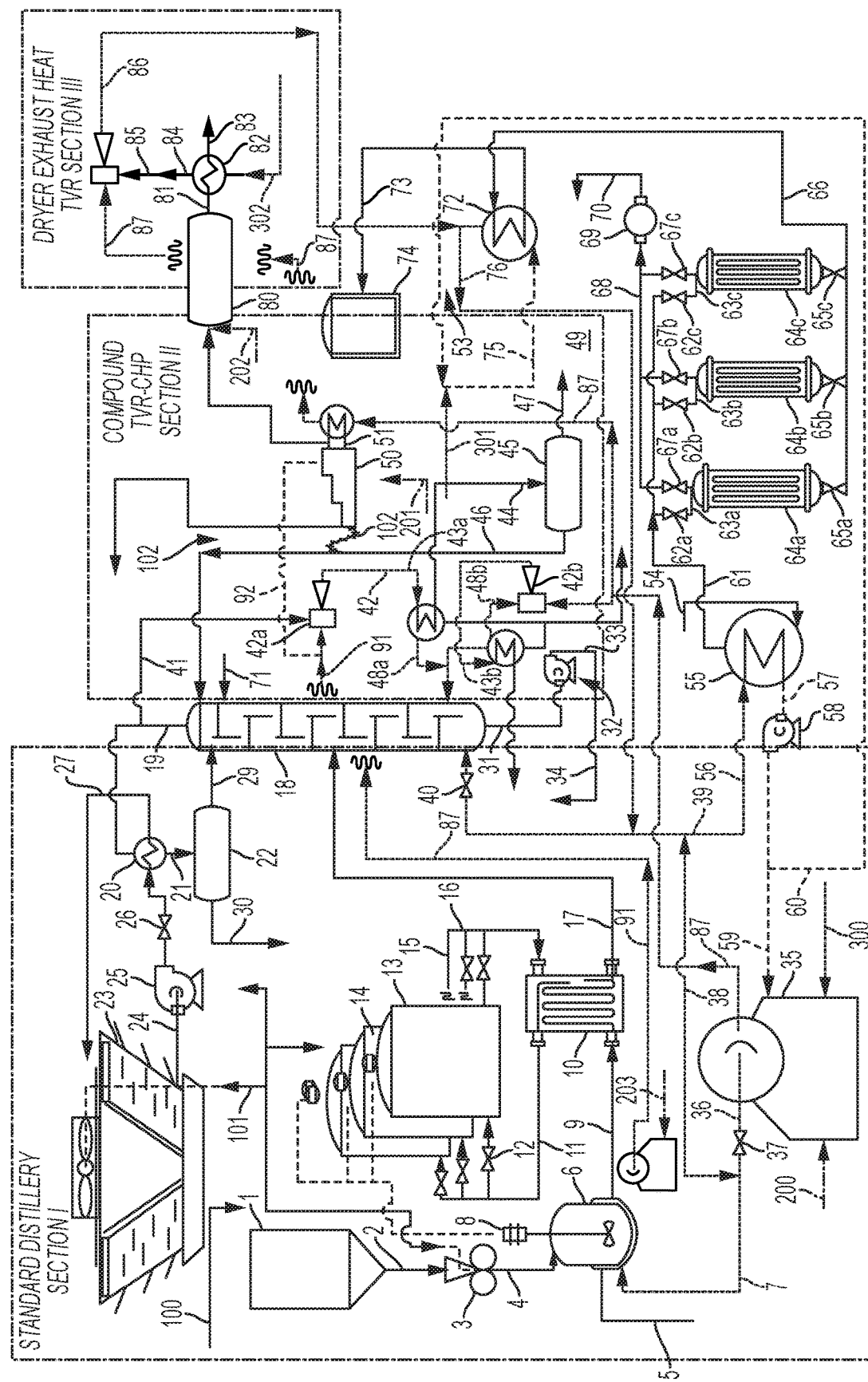

FIG. 7 is a schematic drawing in which Section II depicts a process by which the evaporation-generated steam vapors are passed into the distillation to drive the distillation process, with the resulting alcohol vapors being condensed in the condenser of Section I or passing to the vapor compression of Section II. The evaporator steam passes to compressor stages, with the steam in the compressor stage intake coming from the effect of the evaporator, and the higher-pressure output steam of the compressor passing part of the steam back to the evaporator effect and part to the distillation. The biofuel/biochemical vapors of the distillation process are passed to the intake of a compressor with the higher-pressure biofuel/biochemical vapors passing to a reboiler/evaporator and the generated steam passing to the distillation. In the distillation process, the pressure of the distillation and the high-pressure evaporation effect are operated preferably with the distillation at lower pressure than the evaporation, allowing the distillation alcohol compressed vapor pressure output and the evaporator steam compressed vapor output to have a common pressure to drive the distillation. This integration of distillation vapor compression with evaporation vapor compression is implied for the process configurations together with optional CHP as described in FIGS. 1, 2, 3, and 4.

Figure 8:
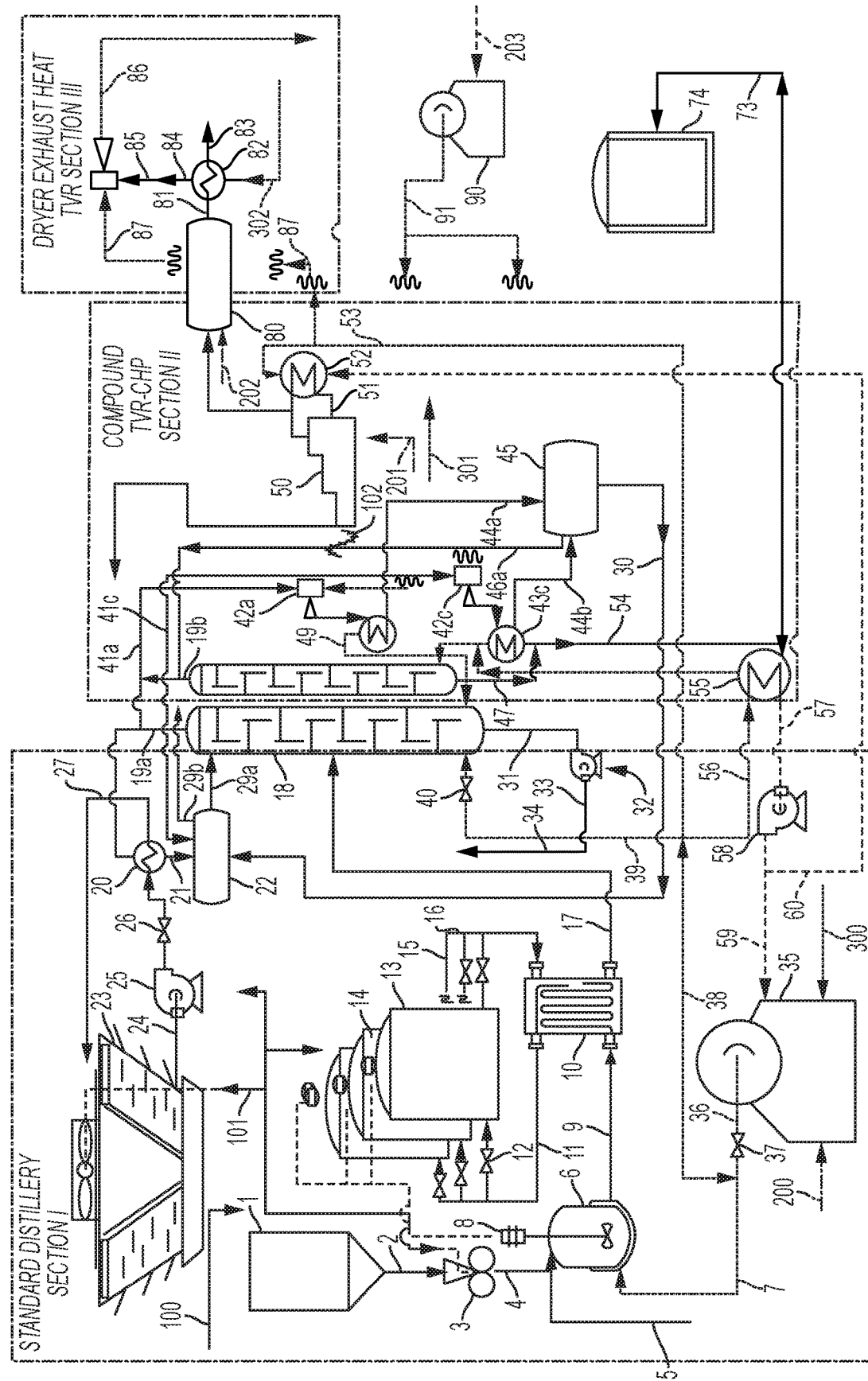

FIG. 8 is a schematic drawing in which Section II depicts a process by which the azeotrope vapors from a two-phase distillation system are being condensing in the condenser of Section I or passing to the vapor compression of Section II. The azeotrope biofuel/biochemical vapors from the two-phase distillation pass into the compressor stages intake, and the higher-pressure output vapors of the compressors pass in part to the condensing side of a reboiler/evaporator which generates steam for the aqueous tower and the other part of the two-phase distillation. The remaining biofuel/biochemical vapors of the distillation process pass to the intake to a compressor, resulting in an output of higher-pressure biofuel/biochemical vapors passing to a second reboiler/organic vaporizer, wherein the generated organic vapors pass to the organic distillation tower. This integration of two-phase distillation with vapor compression driving a reboiler/evaporation for the aqueous distillation and vapor compression also driving the reboiler/organic vaporizer is implied for the process configurations together with optional CHP as described in FIGS. 1, 2, 3, and 4.

Figure 9:
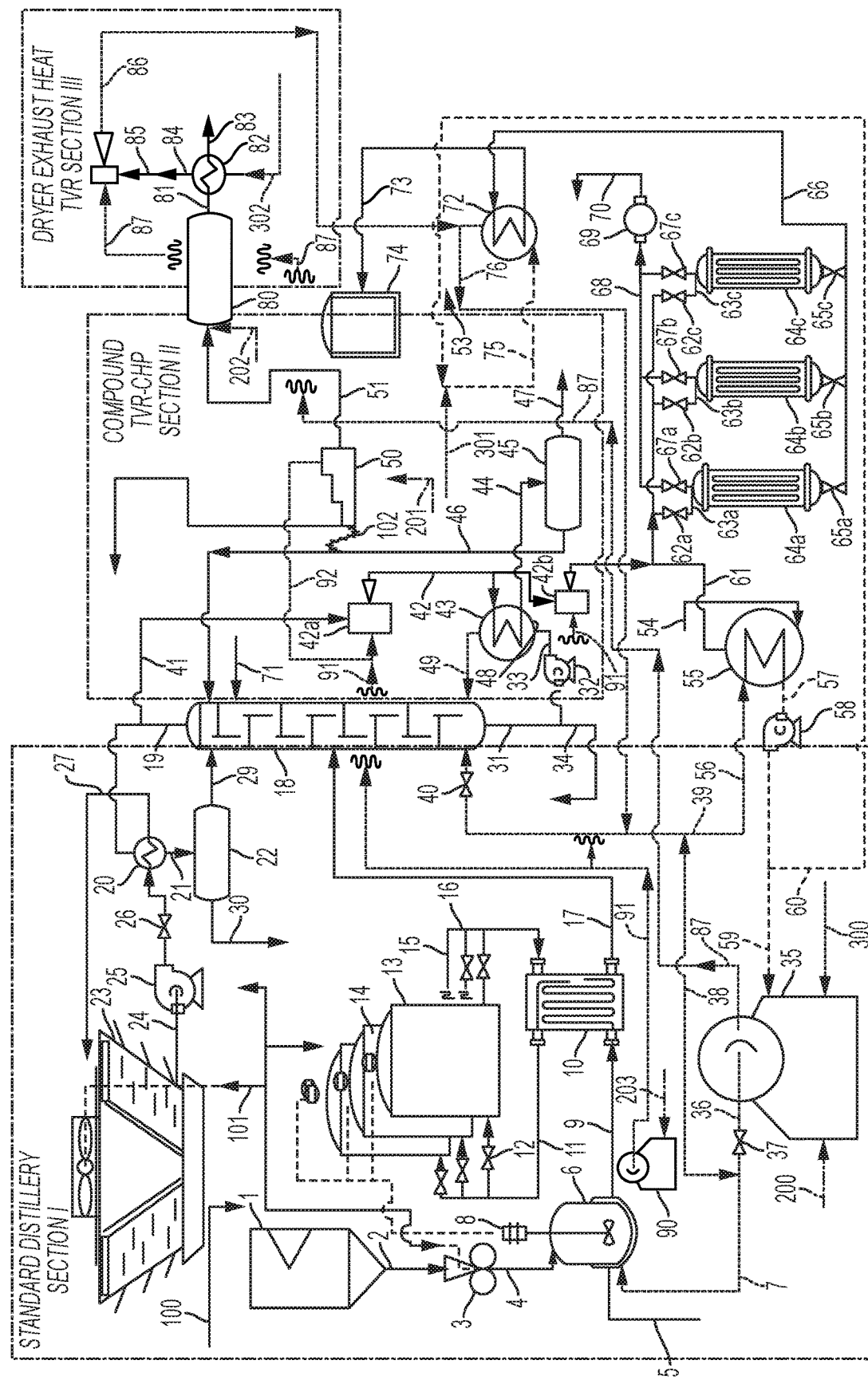

FIG. 9 is a schematic drawing in which Section II depicts a process by which distillation vapors are passed to a vapor compression system, where a portion of the compressed distillation top product vapors pass to a multi-effect evaporation process with the azeotrope biofuel or biochemical vapors condensing. The generated steam is returned to the distillation and the remaining vapors further compressed to the dehydration system, wherein the condensation of the biofuel/biochemical generated steam is returned to drive the biorefinery or distillery. This integration of distillation vapor compression with dehydration vapor compression is implied for the process configurations described in FIGS. 1, 2, 3, 4, 5, 6 and 7.

Figure 10:
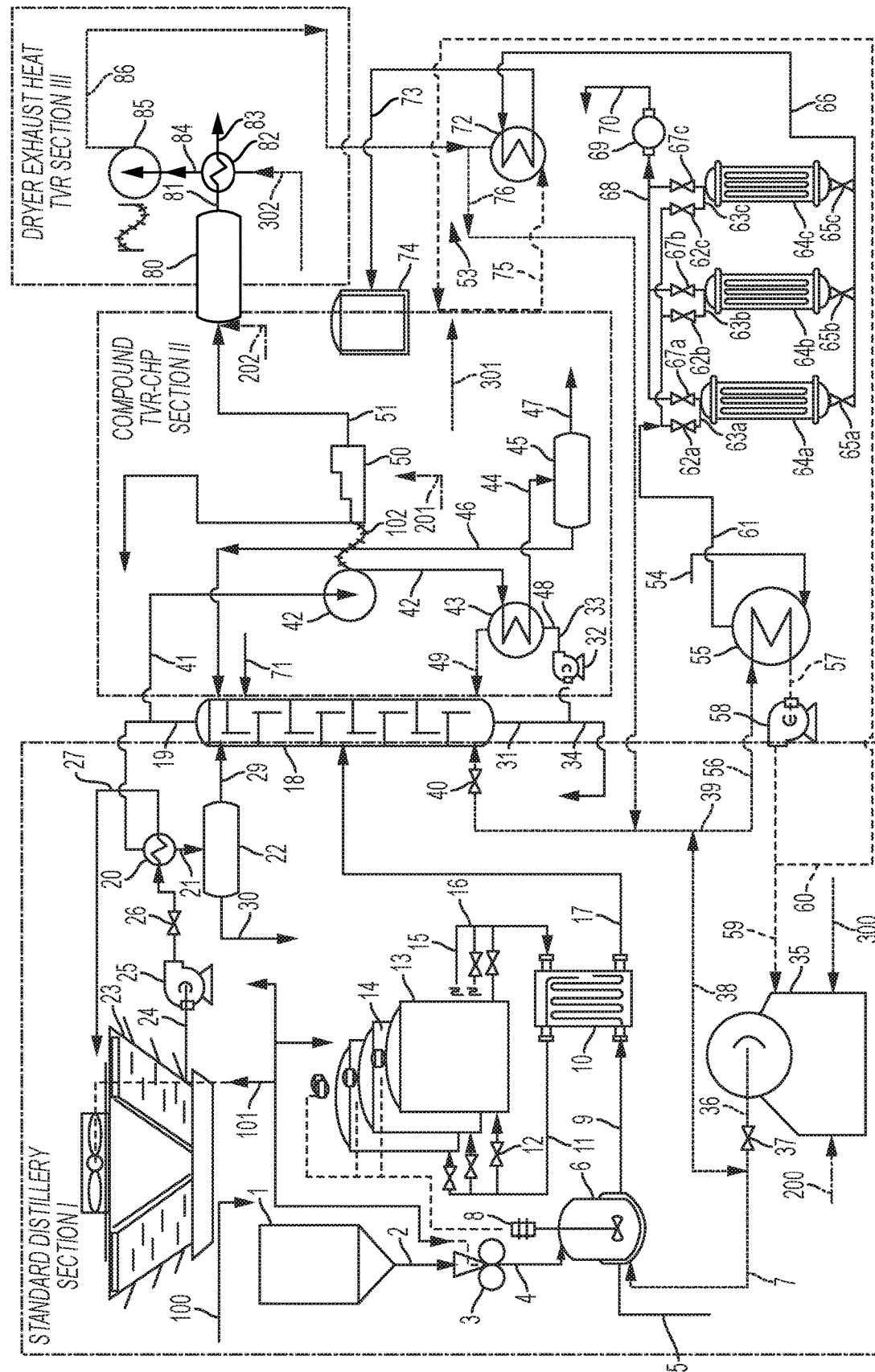
FIG. 10 is a schematic drawing, showing process flows for a distillery or biorefinery, with three hashed boxed areas. The first hashed line area is labeled as "Standard Distillery Section I", the second hashed line area is labeled as "Compound TVR-CHP Section II" or "Compound MVR-CHP Section II", without limitation (Section II may also be referred to as "Compound MVR/TVR-CHP"), and the third hashed line area is labeled as "Dryer Exhaust Heat MVR/TVR Section III", "Dryer Exhaust Heat TVR Section III", or "Dryer Exhaust Heat MVR Section III", without limitation. As explained below, any instance of MVR or TVR may be replaced by TVR or MVR, respectively, in various embodiments.

FIG. 10 is a schematic drawing in which Section III depicts a process by which a portion of the sensible heat and condensable water vapors from the wet cake (stillage) dryer exhaust heat is recaptured to a reboiler-evaporator where the steam passes to a vapor compression system. The compressed steam from the reboiler-evaporator may then be passed to other plant processes. The optional integration of dryer exhaust heat recapture through vapor compression is implied for the process configurations described in FIGS. 1, 2, 3, 4, 5, 6, 7, 8, and 9.

These and other embodiments, features, and advantages of the present invention will become more apparent to those skilled in the art when taken with reference to the following detailed description.

DETAILED DESCRIPTION OF EMBODIMENTS OF THE INVENTION

Certain embodiments of the present invention will now be further described in more detail, in a manner that enables the claimed invention so that a person of ordinary skill in this art can make and use the present invention. All references herein to the "invention" shall be construed to refer to non-limiting embodiments disclosed in this patent application.

Unless otherwise indicated, all numbers expressing conditions, concentrations, yields, and so forth used in the specification and claims are to be understood as being modified in all instances by the term "about." Accordingly, unless indicated to the contrary, the numerical parameters set forth in the following specification and attached claims are approximations that may vary depending at least upon the specific analytical technique. Any numerical value inherently contains certain errors necessarily resulting from the standard deviation found in its respective testing measurements.

As used in this specification and the appended claims, the singular forms "a," "an," and "the" include plural referents unless the context clearly indicates otherwise. Unless defined otherwise, all technical and scientific terms used herein have the same meaning as is commonly understood by one of ordinary skill in the art to which this invention belongs. If a definition set forth in this section is contrary to or otherwise inconsistent with a definition set forth in patents, published patent applications, and other publications that are incorporated by reference, the definition set forth in this specification prevails over the definition that is incorporated herein by reference.

The term "comprising," which is synonymous with "including," "containing," or "characterized by" is inclusive or open-ended and does not exclude additional, unrecited elements or method steps. "Comprising" is a term of art used in claim language which means that the named claim elements are essential, but other claim elements may be added and still form a construct within the scope of the claim.

As used herein, the phrase "consisting of" excludes any element, step, or ingredient not specified in the claim. When the phrase "consists of" (or variations thereof) appears in a clause of the body of a claim, rather than immediately following the preamble, it limits only the element set forth in that clause; other elements are not excluded from the claim as a whole. As used herein, the phrase "consisting essentially of" limits the scope of a claim to the specified elements or method steps, plus those that do not materially affect the basis and novel characteristic(s) of the claimed subject matter.

With respect to the terms "comprising," "consisting of," and "consisting essentially of," where one of these three terms is used herein, the presently disclosed and claimed subject matter may include the use of either of the other two terms. Thus in some embodiments not otherwise explicitly recited, any instance of "comprising" may be replaced by "consisting of" or, alternatively, by "consisting essentially of."

The concept of vapor compression in distillation has been deployed in reducing process requirements in refining for many decades. It has also been widely deployed in water desalination and process evaporation. This method of energy recovery has been rarely utilized, however, in the distillation processes of bio-fermentation producers. In addition, the option of combined heat and power (CHP) has not been widely used in biofuels distilleries as advances in process design have significantly reduced producers' electrical demand to about one-fifth of the total processing energy, reducing incentives.

In this specification, "MVR" means mechanical vapor recompression and "TVR" means thermal vapor recompression. "MVR/TVR" means MVR and/or TVR. All instances of "vapor compression," "vapor recompression," MVR, TVR, MVR/TVR, and the like mean mechanical vapor recompression, thermal vapor recompression, or a combination thereof. Thermal vapor recompression may also be referred to as thermocompression or steam compression.

Some variations of the invention are premised on the realization that the energy consumed in bio-fermentation distillation can be reduced by process and system configurations that recycle distillation heat through the application of vapor compression and combined heat and power methods as disclosed herein. The combination of vapor compression and combined heat and power is preferably configured as a fully redundant retrofit that leverages existing process equipment investment. Compression reduces the total thermal process energy requirement of the plant via recovering the otherwise rejected heats of vaporization, and the mechanical energy required in mechanical compression and/or thermal energy required in thermal compression can be optionally provided from combined heat and power methods. Electrical energy and waste heat of the optional combined heat and power system can be used to offset the plant's electrical demand and process thermal energy requirements.

The invention relates to the combination of distillation, compression, and optionally combined heat and power methods, wherein the total reduction of the purchased electrical and thermal process energy can be optimized through balancing energy usage and conversions, in a manner that minimizes the production energy usage, cost, and environmental impact per gallon of product generated. The ratio of process electrical energy purchased from a power provider or provided through self-generation and the process thermal energy fuel purchased from a supplier may be managed through accounting for the costs of each form of energy relative to the production cost and reduction in usage available from the invention. The invention provides the option of varying the amount of electrical power generated through the optional combined heat and power process to optimize process efficiency using electrical power purchases or self-generation to provide shortfalls or cyclic demands that either exceed the plant's capacity or impose inefficiencies that justify such purchases. The waste heat of a combined heat and power system may be passed as recaptured heat to processes within and outside of the distillation stage.

The invention may, in some instances, utilize provided power and augment or eliminate the optional CHP system. Provided power that is produced as a byproduct of another process or system, or power that better satisfies environmental goals, for example, may be used and the efficiency and cost effectiveness of a CHP system foregone in favor of other benefits. For example, limits on emissions may favor solar, wind, or utility grid provided power. In some cases, very low cost utility grid power that is competitive with CHP power generation costs and reduces the capital costs of the project by eliminating the need for CHP may better meet project economic goals. Minimizing carbon intensity may favor powering the vapor compression with renewable, low carbon-intensity power generation options.

The meaningful and sizable reduction in process thermal energy usage of these plants through addition of the invention will also substantially reduce the carbon intensity ascribed to the plant's process. The distillation energy in a standard bio-fermentation distillery without mechanical vapor compression represents from 40% to 60% of the total process energy. Mechanical vapor compression, when used in distillation, evaporation, dehydration, and drying, recycles latent heat by a closed heat pump, as disclosed for example in U.S. Pat. Nos. 4,340,446, 4,422,903, 4,539,076, 4,645,569, 4,692,218, 4,746,610, 5,294,304, 7,257,945, 8,101,217, 8,101,808, 8,114,255, 8,128,787, 8,283,505, 8,304,588, 8,535,413, and 8,614,077, which are hereby incorporated by reference herein. Thermal vapor compression, when used in distillation, evaporation, dehydration, and drying, recycles latent heat by a closed heat pump, as disclosed for example in U.S. Pat. Nos. 5,772,850, 4,536,258, and 4,585,523, which are hereby incorporated by reference herein.

Distillation is generally the largest consumer of energy in a plant utilizing bio-fermentation due to the necessarily dilute beer produced by micro-organisms. The large amount of water in the beer must be separated from the desired product through distillation. Generally, the distillation system is heated by steam produced from combusting a fuel in a boiler. Vapors collected from the distillation system are cooled in a condenser where they release their latent heat of condensation. This energy is lost to the condenser's cooling water that, in turn, releases its heat to the atmosphere. By rerouting the vapors prior to their introduction into the condenser and increasing the pressure and temperature of the vapors through compression, forcing the superheated vapors to condense in a reboiler, the latent heat of condensation can be captured and transferred to water used to generate steam. This generated steam from the reboiler can be directly recycled to the distillation tower, as described in FIGS. 1, 2, 3, and 4.

In some embodiments, the generated steam from the reboiler may be used to drive an evaporation system wherein pressure drops within the evaporation effects may require additional compression as described in FIG. 5. In some embodiments, the evaporation and distillation may be driven from a common compression system, passing steam to an evaporator operated at a common pressure with the distillation as described in FIG. 6. In some embodiments, the distillation compressor vapors pass to the reboiler as part of the evaporation, passing steam back to the distillation and the evaporation passing steam to the distillation as in FIG. 7. In some embodiments the distillation vapors are partially condensed in the reboiler with the remaining vapors compressed for vapor-phase dehydration with the anhydrous vapor product of dehydration condensing in a reboiler with the generated steam passed back to the distillery or biorefinery. In some embodiments, two-phase distillation compressor azeotrope vapors are balanced between two reboilers with a portion of the vapors condensing in one reboiler for water, which generates steam for driving the aqueous distillation tower, and the remaining compressed vapors passing to another reboiler for the organic alcohol to condense by producing organic vapors for driving the organic distillation tower as in FIG. 8.

In the past, the high cost of driving the vapor compressor limited the economic advantages that could be gained. More efficient motors with integrated heat recapture used for generating electricity to drive electric compressor drive motors or directly driving the compressor have become available, vastly improving process cost and efficiency. Using steam from an existing steam generation system to supplant steam generated through vapor compression can allow the motors to increase their time operating at peak efficiency and provide motive vapors for driving thermal vapor compression. Electricity provided by excess generation not needed for vapor compression can replace electricity formerly supplied by a utility and motor heat recapture can provide additional process heat. Optimizing the efficiency of the motors and using system steam and utility electricity or power provided by any other means to trim output can achieve an optimized system configuration that minimizes total energy usage, cost, and carbon dioxide emissions. System reliability is improved through retention of the existing steam generation and distillation system that can be operated during maintenance of the retrofit vapor compression system.

In a system utilizing mechanical vapor compression, the mechanical energy of the compression is typically equivalent to about 15% to 20% of the thermal energy required for the identical distillation process without compression. The energy advantage in mechanical vapor compression will be typically about 5:1, or in various embodiments, about 3:1, 4:1, 5:1, 6:1, 7:1 or higher. The market values of thermal energy and electricity vary by market with electrical power costs and natural gas thermal energy costs showing a historic cost relationship per unit of energy of 3:1 to 8:1. The relative unit energy price relationship between thermal energy and electrical power determines the economic value of mechanical compression in distillation, evaporation, dehydration, and drying. The investment costs of compression equipment are an additional determinant of the economic advantage of mechanical vapor compression versus thermal vapor compression or standard distillation. High electrical costs for driving the mechanical compression system may outweigh the savings provided by reduced thermal energy demand. Lower capital costs and low thermal energy costs may favor thermal vapor compression.

In a system utilizing thermal vapor compression, the thermal energy of the compression is typically equivalent to about 40% to 70% of the thermal energy required for the identical distillation process without vapor compression. The energy advantage in thermal vapor compression will be typically about 1.5:1, or in various embodiments, about 1.1:1, 1.2:1, 1.3:1, 1.4:1 or higher.

The typically high ratio of electrical power costs per unit energy to thermal natural gas costs per unit energy supports the use of high efficiency combined heat and power in bio-fermentation distillery processing. Electricity can often be generated at a lower cost than the price of power available from local utility providers, and waste heat from the engine is easily directed into the many processes within the plant that require thermal energy not included in the distillation stage. Recently, advances in renewable power generation technologies have encouraged the use of solar and wind generated electricity, as well as waste to energy technologies like gasification and anaerobic digestion, providing options for powering vapor compression systems that may have cost and environmental advantages relative to more traditional power generation technology.

In preferred embodiments, the invention integrates the advantage provided by reducing the cost of mechanical energy through use of the combined heat and power system with the reduced thermal energy required in the distillation system achieved by mechanical vapor compression. The design's optimization is balanced between current energy pricing and expected future trends in energy pricing and environmental regulation. The invention's focus on integration of mechanical vapor compression in distillation, evaporation, dehydration, and drying and combined heat and power provides multiple options for the design and sizing of the major components and uses of the waste heat from the combined heat and power. Several examples are provided to demonstrate possible configurations of the integrated system utilizing mechanical vapor compression in distillation, evaporation, dehydration, and drying and combined heat and power.

Some variations of the present invention provide a method of modifying a distillery or biorefinery, wherein the distillery or biorefinery converts biomass into a biofuel or biochemical, and wherein the biofuel or biochemical is purified by distillation, the method comprising:
  (i) introducing a vapor compression unit comprising a mechanical vapor recompression (MVR) unit and/or a thermal vapor recompression (TVR) unit to recover latent heat and provide a reduction in process thermal energy usage in the distillery or biorefinery; and
  (ii) optionally introducing a combined heat and power (CHP) system having a CHP engine, to provide mechanical, electrical, and/or thermal energy for driving the vapor compression unit, wherein residual waste heat of the CHP engine offsets the process thermal energy usage in the distillery or biorefinery, wherein integration of the vapor compression unit with the optional CHP system is balanced to optimize process energy requirements, process carbon intensity, and/or process energy costs.

Some variations of the present invention provide a method of modifying a distillery or biorefinery, wherein the distillery or biorefinery converts biomass into a biofuel or biochemical, and wherein the biofuel or biochemical is purified by distillation, the method comprising:
  (i) introducing a mechanical vapor recompression (MVR) unit to recover latent heat and provide a reduction in process thermal energy usage in the distillery or biorefinery;
  (ii) introducing a thermal vapor recompression (TVR) unit to further recover latent heat and provide a further reduction in process thermal energy usage in the distillery or biorefinery; and
  (ii) optionally introducing a combined heat and power (CHP) system having a CHP engine, to provide mechanical and electrical energy for driving the MVR unit and thermal energy for driving the TVR unit, wherein residual waste heat of the CHP engine (when the CHP system is present) offsets the process thermal energy usage in the distillery or biorefinery,
wherein integration of the MVR and TVR units with the optional CHP system is balanced to optimize process energy requirements, process carbon intensity, and/or process energy costs.

In some embodiments, the vapor compression unit comprises multiple mechanical or thermal vapor compressors, wherein cascaded heat from the distillation is integrated with multiple stillage evaporations, and wherein compressed biofuel or biochemical vapors and generated steam are returned to the distillation.

In some embodiments, the vapor compression unit comprises multiple mechanical or thermal vapor compressors, wherein cascaded heat from the distillation is integrated with multiple stillage evaporations including a first evaporator, wherein compressed steam from the first evaporator is optionally split between the distillation and a part of the multiple stillage evaporations, and wherein the distillation and at least a portion of the multiple stillage evaporations are operated at equal or near-equal pressure, thereby allowing a compressor stage to cascade heat of evaporation between the distillation and the multiple stillage evaporations.

In some embodiments, the vapor compression unit comprises multiple mechanical or thermal vapor compressors and/or a TVR unit comprising multiple vapor jets, wherein cascaded heat from multiple stillage evaporations to the distillation is integrated with compression of steam from at least one reboiler-evaporator (e.g., from two or more reboiler-evaporators whose output is combined) to drive the distillation and partial evaporation, wherein the distillation and the partial evaporation are operated such that evaporation pressure is higher than distillation pressure, thereby allowing compressor stages to cascade the heat of evaporation into the distillation.

In some embodiments, the vapor compression unit comprises multiple mechanical or thermal vapor compressors, wherein cascaded heat from the distillation is partially recompressed to a reboiler where the condensed distillation top product is recovered for reflux and the remaining vapors are passed to the dehydration, with the pressure of the vapors being sufficient (optionally, additional compressors are used) to raise the pressure as needed to drive the dehydration.

The vapor compression unit may be sized or operated with a standard steam generator to reduce thermal energy required in the distillation, and wherein the standard steam generator is operated at a reduced rate as a result of reduction in steam energy demand due to energy recovered by the vapor compression unit.

The optional CHP engine may be sized or operated in concert with (i) mechanical demand of the MVR unit, if present; (ii) thermal demand of the TVR unit, if present; and (iii) thermal energy demand of the distillery or biorefinery. When a TVR unit is present, at least some of the thermal energy demand of the TVR unit and distillery or biorefinery is optionally provided by waste heat recovered by the CHP system.

The integration of the vapor compression unit with the optional CHP system allows balancing of use in the distillery or biorefinery of process fuel energy and electrical energy unit price. For example, process energy costs may be minimized based on relative market pricing of the process fuel energy and the electrical energy. Optionally, total process energy is not minimized.

The integration of the vapor compression unit with the optional CHP system allows minimization of carbon intensity of the distillery or biorefinery through selective usage of electricity and thermal fuel to minimize total carbon intensity of process energy. In some embodiments, process energy costs are not minimized based on relative market pricing of the process fuel energy and the electrical energy and the individual carbon intensities allocated to thermal and electrical process energy lifecycles.

The present invention also provides a process comprising, or adapted for, any of the disclosed methods. The biofuel or biochemical may be selected from the group consisting of methanol, ethanol, 1-propanol, 2-propanol, n-butanol, isobutanol, 2-butanol, tert-butanol, acetone, and combinations thereof. The biofuel or biochemical may also be selected from organic acids, such as lactic acid, higher alcohols (e.g., $C_{5+}$ alcohols), alkanes, etc. As used herein, "biofuel," "biochemical," biofuel/biochemical" and the like shall refer to one or more fermentation products of interest. Co-products include, but are not limited to, DDG, DDGS, sugars, lignin, still bottoms, and energy.

In addition, the present invention provides systems configured to carry out the disclosed methods. Some variations provide a distillery or biorefinery comprising such a system. The system may be a retrofit to an existing plant. In other embodiments, the biorefinery is a greenfield plant.

In various embodiments, the biomass feedstock may be selected from agricultural crops and/or agricultural residues. In some embodiments, agricultural crops are selected from starch-containing feedstocks, such as corn, wheat, cassava, rice, potato, millet, sorghum, or combinations thereof. In some embodiments, agricultural crops are selected from sucrose-containing feedstocks, such as sugarcane, sugar beets, or combinations thereof.

Lignocellulose biomass may also be used as the biomass feedstock. Lignocellulose biomass includes, for example, plant and plant-derived material, vegetation, agricultural waste, forestry waste, wood waste, paper waste, animal-derived waste, poultry-derived waste, and municipal solid waste. In various embodiments of the invention, the biomass feedstock may include one or more materials selected from: timber harvesting residues, softwood chips, hardwood chips, tree branches, tree stumps, knots, leaves, bark, sawdust, off-spec paper pulp, cellulose, corn, corn stover, wheat straw, rice straw, sugarcane bagasse, switchgrass, *miscanthus*, animal manure, municipal garbage, municipal sewage, commercial waste, grape pumice, almond shells, pecan shells, coconut shells, coffee grounds, grass pellets, hay pellets, wood pellets, cardboard, paper, carbohydrates, plastic, and cloth. Mixtures of starch-containing and/or sucrose-containing feedstocks with cellulosic feedstocks, for example, may be used.

Some variations provide an energy-efficient system configured for a distillery or biorefinery, wherein the distillery or biorefinery is capable of converting biomass into a biofuel or biochemical, and wherein the distillery or biorefinery includes distillation configured to purify the biofuel or biochemical, the system comprising:
  (i) a vapor compression unit comprising a mechanical vapor recompression (MVR) sub-system and/or a thermal vapor recompression (TVR) sub-system configured to recover the latent heat in distillation, evaporation, dehydration, and/or drying and to provide a reduction in process thermal energy usage in the distillery or biorefinery; and
  (ii) optionally a combined heat and power (CHP) sub-system having a CHP engine, configured to provide mechanical, electrical, and/or thermal energy for driving the vapor compression unit, wherein the optional CHP sub-system and the vapor compression unit are integrated and configured so that residual waste heat of the CHP engine offsets process thermal energy usage in the distillery or biorefinery.

Some variations provide an energy-efficient system configured for a distillery or biorefinery, wherein the distillery or biorefinery is capable of converting biomass into a biofuel or biochemical, and wherein the distillery or biorefinery includes distillation configured to purify the biofuel or biochemical, the system comprising:
  (i) a mechanical vapor recompression (MVR) sub-system configured to recover latent heat in distillation, evaporation, dehydration, and/or drying and to provide a reduction in process thermal energy usage in the distillery or biorefinery;
  (ii) a thermal vapor recompression (TVR) sub-system configured to recover latent heat in distillation, evaporation, dehydration, and/or drying and to provide a further reduction in process thermal energy usage in the distillery or biorefinery; and
  (iii) optionally a combined heat and power (CHP) sub-system having a CHP engine, configured to provide mechanical and electrical energy for driving the MVR unit and thermal energy for driving the TVR unit, wherein the optional CHP sub-system with MVR and TVR units are integrated and configured so that residual waste heat of the CHP engine offsets process thermal energy usage in the distillery or biorefinery.

In some embodiments, the vapor compression unit comprises multiple MVR and/or TVR compressors, wherein cascaded heat from the distillation is integrated with multiple stillage evaporations, and wherein compressed biofuel or biochemical vapors and generated steam are returned to the distillation within the system.

In certain embodiments, the vapor compression unit comprises multiple MVR and/or TVR compressors, wherein cascaded heat from the distillation is integrated with multiple stillage evaporations including a first evaporator, wherein compressed steam from the first evaporator is optionally split between the distillation and a part of the multiple stillage evaporations, and wherein a compressor stage is configured to cascade heat of evaporation between the distillation and the multiple stillage evaporations.

In some embodiments, the vapor compression unit comprises multiple MVR and/or TVR, wherein cascaded heat from multiple stillage evaporations to the distillation is integrated with compression of steam from at least one reboiler-evaporator to drive the distillation and partial evaporation, and wherein compressor stages are configured to cascade the heat of evaporation into the distillation.

An MVR unit may be configured with a standard steam generator to reduce thermal energy required in the distillation. The optional CHP engine may be sized in concert with (i) mechanical demand of the MVR unit and (ii) thermal energy demand of the distillery or biorefinery. The waste heat recovered by a CHP system optionally provides at least some of the thermal energy demand of the distillery or biorefinery, and may drive an optional TVR unit when present in conjunction with the MVR unit.

A TVR unit may be configured with a standard steam generator to reduce thermal energy required in the distillation. The optional CHP engine may be sized in concert with (i) thermal demand of the TVR unit and (ii) thermal energy demand of the distillery or biorefinery. The waste heat recovered by a CHP system optionally provides at least some of the motive vapor to drive a TVR vapor jet and/or provide thermal energy demand of the distillery or biorefinery.

The terms "distillery," "distillery process," and "distillery plant" herein refer to a bio-fermentation plant or process in which raw biomass is processed through stages leading to a fermentation stage and on to separation of the fermentation products using distillation separation, evaporation, and dehydration as at least one stage for product purification. The term "biorefinery" herein refers to a plant or process in which raw biomass is processed through stages leading to a fermentation stage and on to separation of the fermentation products using distillation separation as at least one stage for product purification, wherein the fermentation product may be any biofuel or biochemical, and wherein the biomass feedstock may be lignocellulosic biomass. All instances of "distillery" in this specification may be replaced with "biorefinery," and vice-versa, in some embodiments.

The term "total process energy" herein refers to the thermal energy required to raise process steam by burning fuels, or direct heating of processes by burning fuels, plus the electrical energy required for mechanical power used in pumping, stirring, grinding, etc.

The terms "addition of mechanical vapor compression in distillation, evaporation, dehydration, and drying" and "addition of combined heat and power" herein refer to a retrofit or augmentation of a standard distillery or biorefinery that uses a standard thermally driven distillation process, to a distillery or biorefinery enhanced with the option of diverting vapors into a mechanical vapor compression system integrated into the distillery or biorefinery, including a combined heat and power system.

The terms "mechanical vapor compression in distillation, evaporation, dehydration, and drying", "thermal vapor compression in distillation, evaporation, dehydration, and drying" and "integrated combined heat and power" herein refer to the addition of mechanical vapor compression, vapor jet compression and combined heat and power, respectively, to provide the ability to operate with various combinations of mechanical vapor compression and/or thermal vapor compression, standard process steam generated by the original system, and combined heat and power to receive the maximum advantage from each of the added processes (i.e., mechanical vapor compression and/or thermal vapor compression in distillation, evaporation, dehydration, and drying, and combined heat and power).

The terms "bio-fermentation distillery process stages," as found in each of the schematic flow diagrams (FIGS. 1, 2, 3, 4, 5, 6, 7, 8, 9, and 10) herein, refer generally to stages 1 through 9 as follows:

Stage 1: A milling stage or device(s) which process biomass by physically dividing the feedstock materials with a grinding or extrusion process which exposes the internal parts of the feedstock;

Stage 2: A cooking stage which uses various combinations of controlled temperatures, pressures, stirring, and special chemical conditioning with acidic or basic chemicals, and/or enzymes (e.g., amylase or cellulase enzymes), for breaking polysaccharides into glucosides;

Stage 3: A heat exchanger stage which cools the cook solution to fermentation temperatures and conversely heats post-fermentation products up to distillation temperatures;

Stage 4: A fermentation stage wherein the cook solution has biological agents introduced to ferment the sugars to the desired biochemical product(s);

Stage 5: A distillation stage, after the fermented products have been pre-heated in the heat exchanger of stage 3, where the biochemical top products are separated from the fermentation waters;

Stage 6: A condensation stage where the vapors from the distillation stage 5 are passed on to a cooling system where the latent heat is discarded, or where the vapors are mechanically compressed to recover the latent heat and cascade the heat to, or from, stages 7 and stage 8;

Stage 7: A stillage handling stage for the bottom product of the distillation or aqueous distillation stage 5, for recovering wet co-products of the fermentation to be further processed with possible drying and, potentially, evaporation to concentrate thin stillage;

Stage 8: An optional dehydration stage for the biochemical products from the distillation stage 5, if the distillation stage 5 does not sufficiently separate the biochemicals from the fermentation water to reach the desired purity; and Stage 9: An optional storage stage where the high-grade biochemical goes to storage, if the biochemical product is not immediately shipped from the plant (e.g., if not directly pumped into tank trucks or rail cars).

Herein the "general distillery process" refers in total to mean the many stages which all require energy in the form of thermal/steam or mechanical/electrical, wherein the thermal and mechanical energy is in part or in full supplied by a combined heat and power plant. The portion of the energy that is not provided from the combined heat and power plant is derived from purchased or self-generated power or fuel from a supplier as will be found in a plant without mechanical vapor compression in distillation, evaporation, dehydration, and drying and/or without combined heat and power, or in the case where the vapor compression in distillation, evaporation, dehydration, and drying and/or combined heat and power are not being used.

The process energy distribution in the distillery depends on the aforementioned stages 1 through stage 9, with the exception of the distillation as stage 5, wherein the use of the mechanical vapor compression reduces the thermal-steam energy for the distillation, evaporation, and optionally dehydration. Distillation normally represents the largest energy-consuming stage in the distillery and therefore provides the largest potential opportunity for reducing the total energy of the process. With the exception of the mechanical and thermal energy demand of the distillation in stage 5, the other stages require lesser amounts of mechanical energy and/or thermal energy which may be met by the combined heat and power system.

Examples of the different options available to supply the thermal-mechanical energy produced from the combined heat and power system to the distillery and dryer are shown in the ten schematic drawings in FIGS. 1, 2, 3, 4, 5, 6, 7, 8, 9, and 10. The thermal and mechanical-electrical distribution of the heat and power is proposed in varied uses for the distillery stages. In these drawings, like numerals refer to like apparatus, streams, or unit operations.

The invention in some embodiments is shown in FIGS. 1, 2, 3, 4, 5, 6, 7, 8, 9, and 10, having a common process path with the process effluent flow beginning with the raw biomass being stored in a bin 1, which delivers the biomass substrate via delivery duct 2 to a milling/extrusion process 3, which renders the substrate to a biomass flour having a suitable size so that the internal portions of the raw biomass are exposed for chemical conversion and processing. The biomass flour passes by a duct 4 with additional chemicals, which may include for example acids or enzymatic agents, and ultimately to the cooking process in vessel 6.

The biomass flour passing from the duct 4 is mixed with process water by a process line 5, where the mixed flour and process water enters the cooking vessel 6. Within the cooking vessel 6, the application of temperature/pressure is delivered by a process steam line 7, and chemicals in a cooking vessel 6, proceeding with the chemical conversion to fermentable saccharides with the assistance of a stirring system 8.

The product of chemically converted slurry from the cooking vessel 6, passes via process line 9, to a heat exchanger 10, where the heat invested into the cook process is removed prior to the fermentation, since the fermentation typically occurs at lower temperatures than cooking. The cook slurry, after being cooled in the heat exchanger 10, is transported by a process line 11 which is controlled via a valve system 12, where the cook slurry passes to a battery of fermenters 13, which may be configured as a batch or continuous fermentation system, with a stirring system 14.

The finished fermentation product, that contains the desired biochemical product as a watery solution with other side products, passes via a valve controlled line 15, to process line 16, where the biochemical product of the fermentation is heated via heat exchanger 10, that passes heat from the high-temperature cook slurry going into the fermentation system to the fermentation product leaving the fermentation system passing via a process line 17, to the distillation system 18 (FIGS. 1 through 7) or 18a (aqueous distillation system, FIG. 8). In FIG. 8, the distillation system 18(*a,b*) includes an aqueous distillation system 18a and an organic distillation system 18b.

The distillation system 18 or 18(*a,b*) further processes the watery fermented solution to further separate desired biochemical products from the water. The distillation system 18 or 18(*a,b*) yields a top product which has a biochemical product composition that in some embodiments approaches an azeotrope with water, or which may be near purity with respect to the desired biochemical. The azeotrope or nearly pure biochemical product passes out of the distillation system as vapors via a vapor line(s) 19 or 19(a,b). The distillation vapor line(s) 19 or 19(a,b) leads to two different process paths. The existing process path is labeled "Section I." The retrofit or enhancement systems are labeled "Section II" and "Section III".

In Section I, the vapors pass to a standard distillation condenser 20, with the condensed distillation top product passing via liquid line 21 to a holding reflux tank 22 (reflux tank in FIG. 1 through FIG. 7 and FIG. 9, and phase-separation tank in FIG. 8).

The distillation condenser system 20 is cooled by a cooling system 23, (cooling tower). The cooling water from the cooling system 20 passes via a pipe 24 to a circulation pump 25, which pumps the cooling water by a valve controlled pipe 26, to the condenser 20, after which the cooling water is returned via a pipe 27 to the cooling system 23.

The distillation top product leaving the condenser passes via the liquid line 29(a,b) to the reflux tank/buffer and then to the distillation system 18(a,b) as the reflux. At least a portion of the top product, as a single-phase azeotrope (as in FIGS. 1 through 7 and 9), passes back to the distillation 18. In some embodiments, at least a portion of a phase-separable azeotrope (as in FIG. 8) passes as the total top product, via two separate streams based on the phase separation, passing back to the distillation towers; the heavy aqueous phase passes to the aqueous distillation 18a via liquid line 29a and the light organic phase passes to the organic distillation 18b via liquid line 29b. The single-phase examples in FIG. 1 through FIG. 7 and FIG. 9 have the remainder of the condensed distillation top product from the distillation system 18 which is not passed as reflux is the final product, pure or near-pure biochemical or an azeotrope with water that passes via a liquid line 30 to the dehydration system 54.

The bottom product of the distillation system, 18 or 18(a), which contains the heavy components as stillage, passes via a liquid line 31, to a pump 32, where the liquid passes via a line 33, which leads to two potential paths wherein it is split between the final bottom product via a liquid line 33, or cycled through a reboiler-condenser(s) 43(a,b) via a liquid line(s) 48(a,b), with the difference passing away from the distillation system, 18 or 18(a), via a liquid line 34, wherein the stillage is optionally further processed to recover co-products having commercial value. Thin stillage is returned to the reboilers 43(a) and 43(b), resulting in thin stillage passing to lines 48(d) and 48(e), and the reboiler condensate from the generated steam passing as condensate to the cook stage via line 48(c).

The distillation system, 18 or 18(a,b), may in part be driven thermally by a steam generator 35, wherein the production steam passes via a steam line 36, with a control valve 37, potentially serving other thermal demands in the system such as steam line 7 to the cook process. The steam generator 35 is fueled via fuel line 200. The bidirectional steam line 38 forms a connection between the steam generator 35 and the potential waste heat from the combined heat and power system 52 via a steam line 53. The steam line 39 is controlled by a valve 40 to deliver steam to potentially drive the distillation system, 18(a).

In Section II, the top product of the distillation system, 18 or 18(a,b), passes via a vapor line(s), 19 or 19(a,b), which is potentially split with the condenser system 20, passing to an optional vapor line 41(a) for single-phase distillation or 41a and 41b for two-phase distillation system, then passing to a compressor 42(a) for single-phase distillation or 42a and 42b for two-phase distillation. The compressor(s) 42(a, b) receives mechanical energy from an engine driver 50, receiving fuel via line 201 that produces mechanical-electrical energy to meet the demand of the compressor(s) and/or the electrical demand in the plant's processes, or motive vapor energy via steam/vapor line 87.

In FIG. 5, the compressor 42(a) compresses the biofuel/biochemical-rich distillate vapors that pass through vapor line 42. The compressed vapors pass to a reboiler-condenser 43(a), where they condense at a higher temperature than the stillage bottom products of the distillation 18, pumped by pump 33 via a liquid line 48(a) to the reboiler-condenser 43(a). The stillage bottom product boils in the reboiler-condenser 43(a), forming steam with the steam passing via a steam line 49, to drive and meet the thermal demand of the distillation system 18.

In FIG. 9, the compressor 42a compresses a portion of the biofuel/biochemical-rich distillate vapors that pass to a reboiler-condenser 43a, where they condense at a higher temperature than the stillage bottom products of the distillation 18 with the remaining biofuel/biochemical-rich distillate vapors passing to an optional compressor 42b and then passing to the dehydration vapor line 61 to vapor-phase dehydration.

The reboiler-condenser(s) 43 or 43(a) condensate for single-phase distillation in FIGS. 1 through 7 and 9, and reboiler-condenser(s) 43a and 43c condensate for phase-separated distillation in FIG. 8, as near-pure biochemical or azeotrope, passes via liquid line 44 to a compression-side reflux tank 45 in FIG. 1 through FIG. 7 and FIG. 9 or phase-separation tank 45 in FIG. 8. The condensed pure or azeotrope biochemical product passes via liquid line 46 to the distillation system 18 as reflux, with the remainder being final top product for single-phase distillation in FIG. 1 through FIG. 7 and FIG. 9 or reflux to 18b in two-phase distillation in FIG. 8 via line 46. The condensate of the two-phase azeotropes separate with the light liquid via line 46 to organic distillation tower 18b, and the heavy aqueous mixture to the aqueous distillation tower 18a via liquid line 30.

The single-phase distillation in FIG. 1 through FIG. 7 and FIG. 9 having the compressor side reflux tank 45 passes the residual condensate as final distillation top product via liquid line 47, to the dehydration system 54 where FIG. 9 may pass all final biofuel or biochemical to the dehydration as compressed vapors via 42b to vapor line 61.

The two-phase distillation system example in FIG. 8 passes the final biochemical bottom product from the organic distillation tower 18b, via liquid line 47, passing to reboiler 43c (reboiler/organic vaporizer) and via liquid line 54, passing to reboiler 55. The organic vapors generated in the reboiler 43c, pass to the organic distillation tower 18b via the vapor line 46, and from reboiler 55, the vapors are passed to organic distillation tower 18b the vapor line 61. The remaining final biochemical product not passing to the reboilers, 42c and 55, passes via the liquid line 73, to the biochemical storage tank 74.

The engine driving the combined heat and power system 50 generates mechanical power for the compressor(s) and/or thermal energy for the motive vapors for the vapor jet via line 91, 42(a,b,c), and electrical power for the distillery system via electrical generator 102. The waste heat from the engine provides a source of thermal energy to drive the distillery, via a heat duct 51.

The vapor generator 90 produces vapors, passing via line 91, for driving the thermal vapor compressor 42. The waste heat from the engine provides a source for thermal energy to drive the thermal vapor compressor 42 via line 92, and thermal source to drive the distillery, via line 51.

The waste heat from the combined heat and power system 50 passes via a piping/duct system 51, to a point where the heat is used directly or it passes to a heat exchanger 52. The heat exchanger 52 may generate steam from a heat recovery steam generator (HRSG), wherein recovered heat as steam passes via steam line 51, and wherein the produced steam goes to meet steam demands throughout the distillery via the steam line 53. Steam line 53 connects to steam line 39 going to the distillation system, 18(*a*).

Steam line 38 connects to steam line 7 that drives the cook tank 6 and connects to steam line 56 that drives the azeotrope dehydration vaporizer 55. Thereby, the waste heat from the combined heat and power system 50 provides the thermal energy required in the cook process, the distillation process, and/or the dehydration system.

The single-phase distillation top product, for FIG. 1 through FIG. 7, passes via liquid lines 30 and 47—when an azeotrope requires further removal of water to reach the desired biochemical product quality—to a pressure-swing vapor-phase molecular sieve dehydration or other final dehydration system. This system receives the azeotrope product via line 54. The liquid or vapor azeotrope product moving to the dehydration system from the distillation should be vaporized or superheated vapors at an increased pressure, which occurs in the heat exchanger 55 (steam-driven organic vaporizer). The steam via line 56 condenses as the azeotrope vaporizes or superheats via line 54, wherein the azeotrope vapors pass via vapor line 61 to the dehydration system. The process steam which drives the vaporizer heat exchanger 55 condenses and the liquid condensate is recycled to the steam generator 35, and/or to the waste heat—driven steam generator (HRSG) 53 via condensate line 57 passing to recycle pump 58. The recycle condensate passes to the steam generator 35 via condensate line 59 and/or moves via condensate line 60 to the waste heat—driven HRSG 52.

The two-phase distillation, as for FIG. 8, passes the final organic product from the organic distillation tower 18(*b*) via liquid line 47. The final product passes to reboiler 43*c* (reboiler/organic vaporizer) wherein vapors are produced to drive the organic distillation tower 18*b* via the vapor line 46*c*, with the remainder of the organic product passes to the liquid line 54. The final organic liquid product moving via line 54 passes to a reboiler 55 (steam-driven organic vaporizer) which generates vapors that pass via vapor line 46*b*, which passes vapors to vapor line 46*c*, which passes the vapors to the organic distillation tower 18*b*. The process steam which drives the vaporizer heat exchanger 55 condenses and the liquid condensate is recycled to the steam generator 35, and/or to the waste heat—driven steam generator (HRSG) 53, via condensate line 57 passing to recycle pump 58. The recycle condensate passes to the steam generator 35, via condensate line 59 and/or moves via condensate line 60 to the waste heat—driven HRSG 52.

In the FIG. 1 through FIG. 7 and FIG. 9 single-phase distillation systems, which produce azeotropes with excessive water, the pressurized azeotrope distillation top product is passed to the vapor-phase dehydration system. The dehydration system is depicted as a three-bottle system, although the number of bottles may be two or greater. The described dehydration system passes the pressurized vapors via a three-valve system wherein one of the bottles is in dehydration mode while the two alternative bottles are being regenerated under low pressure. The three bottles are cycled in a round-robin style with each bottle being used for a period based on the capacity of the dehydration medium, while the alternative bottles are regenerating through application of a vacuum to recover the captured water. A portion of the dehydrated product is used to backflush the regenerated bottles, so the regenerated bottle can be placed back in service when the captured water is removed.

The dehydration system, in FIG. 1 through FIG. 7 and FIG. 9, passes the pressurized vapors via vapor line 61 to a system of control valves, 62*a*/62*b*/62*c*, wherein an open valve passes the pressurized vapors to the appropriate vapor line, 63*a*/63*b*/63*c*, which passes the product to the dehydrating bottle, 64*a*/64*b*/64*c*, that is in service during that period of operation. The dehydrated product passes through the dehydrating bottle via the exiting control valves, 65*a*/65*b*/65*c*, to vapor line 66 as the anhydrous biochemical product.

The dehydration bottles being regenerated pass a fraction of the dehydrated vapors from the one active bottle to backflush the regenerating bottles. The low-pressure bottle is controlled by control valves, 67*a*/67*b*/67*c*, with the regeneration vapors containing a mixture of the regenerated water vapors and the backflush anhydrous product passing via the vapor line 68. The regeneration is driven by a vacuum pump system 69, wherein the vapors are pumped via line 70. The dehydration regeneration product is returned to the distillation system 18 via line 71 for re-distillation of the regeneration product containing the backflush product.

The final anhydrous biochemical product from the dehydration passes as a vapor to an anhydrous condenser reboiler 72, wherein the final product is condensed and passed via liquid line 73 to storage tank 74 (e.g., anhydrous biochemical tank). The anhydrous condenser is cooled by the condenser water via condensate water line 75, wherein the heated water is vaporized to steam in the reboiler 72, with the steam passed via line steam line 75, and wherein the steam may be used to drive the thermal demands of the distillery.

The process steam boiler 35 has makeup water added into the condensate return line 60 and/or 75, via the water lines 300 and/or 301.

In section III, the dryer drum 80 receives drying heat via heated exhaust from combustion burners or a heated drum. The water vapor-laden dryer exhaust gases pass through line 81, connected to reboiler-evaporator 82 feed makeup water from line 302, that recaptures waste heat from the exhaust gases, with partial condensation where the condensate passes via line 83 as process water. The makeup water in reboiler-evaporator 82 boils, forming low-pressure steam which passes via line 84 to compressor 85, as depicted in FIG. 1, FIG. 2, FIG. 3, FIG. 4, FIG. 5, FIG. 6, FIG. 7, FIG. 8, FIG. 9 and FIG. 10, or vapor jet 85 driven by motive steam generated from steam generator 35 via line 87, which raises the pressure and/or temperature of the steam passing to process steam line 76 via line 86 for use in meeting plant process requirements.

Purchased or self-generated electrical power 100 is used to meet the process electrical demand for the milling/extrusion, cook stirring, fermentation stirring, and pumping, 101. The combined heat and power system 50, which consumes fuel via line 201, generates electrical power 102, which offsets other electrical power requirements 100. The thermal energy captured from the combined heat and power system 50 generates steam via the HRSG 52, which offsets the fuel consumed in the steam generator 35 provided fuel via line 200. The portion of recovered waste heat from the combined heat and power via line 201 reduces the fuel 200 required in the steam generator 35.

The combined heat and power system provides local mechanical/electrical energy 201, and recovered waste thermal energy 52, wherein the mechanical/electrical demands of the distillery can be met through the use of local energy production via power line 102. The mechanical energy consumed in the mechanical vapor compression compressor 42 reduces the thermal energy demand of the distillery by reducing the steam demand in steam line 40 to the distillation 18, and/or thermal vapor compression by vapor jet 42 reduces the thermal energy demand of the distillery in line 40 to distillation 18. When Compound MVR-CHP Section II is operated, a large portion of the steam formerly or otherwise produced by consuming the fuel 200, in the steam generator 35, is provided by steam generated from heat recaptured in reboiler(s) 43(*a,b*) that would otherwise be lost to cooling tower 23 in Standard Distillery Section I standard operations. Operating Section II provides a net reduction in both fuel required 200 and electrical power 100. Fuel consumed in the engine/CHP drives the compressor(s) 42(*a, b*), and generates excess electrical power 102 to meet plant needs, offsetting electrical power 100 previously or otherwise purchased to meet plant demand—yielding a reduction in energy demand for both fuel and electrical power.

The example of FIG. 1 preferably sizes the combined heat and power system to produce mechanical and electrical energy to drive the mechanical vapor compression in stage 5, referring to the above-describes stages 1 through 9. The thermal energy of the distillation is greatly reduced, and the electrical energy beyond the amount required to drive the compressor of the vapor compression system, is used to generate electrical power. This electrical power serves the electrical demand of the other stages which require mechanical energy such as pumping, stirring as in the cooking in stage 2, and fermentation in stage 4. FIG. 1 shows heat from the combined heat and power system used to generate steam by heat recovery with steam generation, in which the steam is passed on to potentially all other thermally intensive stages such as the cook in stage 2, the distillation in stage 5 and in stage 7 for co-product drying (for any steam not offset by the mechanical vapor compression), and/or the dehydration in stage 8. Through this approach, the combined heat and power may be sized to provide mechanical energy as needed in the vapor compression with the residual power offsetting the otherwise more expensive electrical costs of the distillery stages. The resulting waste heat meets, but does not exceed, the other thermal-steam demands of heat-intensive stages.

The example of FIG. 2, like FIG. 1, shows the distribution of heat from the optional combined heat and power system used to produce mechanical and electrical energy to drive the mechanical vapor compression in stage 5, wherein the thermal energy of the distillation is greatly reduced, and the electrical energy beyond the demand to drive the compressor of the vapor compression is used to generate electrical power which goes to serve the electrical demand of the other stages which require mechanical energy such as pumping, stirring (as in the cooking in stage 2) and fermentation in stage 4. FIG. 2 shows a split of the heat from the combined heat and power system used to generate steam by heat recovery with steam generation, wherein the steam is passed on to potentially all other thermally intensive stages, such as the cook in stage 2, the distillation in stage 5 (for any steam not offset by the mechanical vapor compression), and/or the dehydration in stage 8. Part of the waste heat of the combined heat and power system may be passed on to directly dry co-products of the distillery stillage in stage 7, and generate steam from the recovered heat from exhaust gases through vapor compression.

The example of FIG. 3 like FIG. 1 and FIG. 2 shows the distribution of the heat from the optional combined heat and power system used to produce mechanical and electrical energy to drive the mechanical vapor compression in stage 5, wherein the thermal energy of the distillation is greatly reduced, and the electrical energy beyond the amount needed to drive the compressor of the vapor compression serves the electrical demand of the other stages which require mechanical energy such as pumping, stirring as in the cooking in stage 2, and fermentation in stage 4. FIG. 3 shows the heat from the combined heat and power system used to directly preheat process water by using the heated cooling water from the power system, or by preheating the process water with a combination of direct and out-of-contact heat exchange, wherein the cook in stage 2 has reduced thermal demand and/or using the power system waste heat to directly dry co-products of the distillery stillage in stage 7, and generate steam from the recovered heat from exhaust gases through vapor compression.

The example of FIG. 4 like FIG. 1 and FIG. 2 shows the distribution of the heat from the optional combined heat and power system used to produce mechanical and electrical energy to drive the mechanical vapor compression in stage 5, wherein the thermal energy of the distillation is greatly reduced and the electrical energy may be less than or equal to the amount needed to drive the compressor of the vapor compression system, leaving little or no residual electrical to serve the electrical demand of the other stages which require mechanical energy such as pumping, stirring as in the cooking in stage 2, and fermentation in stage 4. FIG. 4 shows the heat from the combined heat and power system used to generate steam by heat recovery with steam generation, wherein the steam is then passed through a steam turbine which generates electricity with the low pressure stage of the turbine passing the exhaust steam on to potentially all other thermally intensive stages, such as the cook in stage 2, the distillation in stage 5 (for any steam not offset by the mechanical vapor compression), and the dehydration in stage 8, and the steam turbine electrical power is used to meet the electrical power demand of the other stages which require mechanical energy such as pumping, stirring as in the cooking in stage 2, and fermentation in stage 4.

The examples of FIG. 5 and FIG. 6, like FIGS. 1, 2, 3, and 4, show the distribution of the heat from the optional combined heat and power system used to produce mechanical and electrical energy to drive the mechanical vapor compression in stage 5 and stage 7, wherein the thermal energy of distillation and evaporation are greatly reduced and the electrical energy generated may be less than or equal to the amount needed to drive the compressor of the vapor compression system, leaving little or no residual electrical to serve the electrical demand of the other stages which require mechanical energy such as pumping, stirring as in the cooking in stage 2, and fermentation in stage 4. FIG. 5 shows the distillation in stage 5 by compression passes the latent heat on to a multi-effect evaporation in stage 7 for the concentration of the thin stillage bottoms from stage 5, and the cascaded steam from the final evaporation effect is part of the mechanical vapor compression that recycles the steam back to distillation stage 5. The waste heat from the combined heat and power is distributed to meet the thermal demands of a cook process stage 2, distillation stage 5, drying stage 7 by generated steam from the recovered heat of exhaust gases through vapor compression, and dehydration stage 8.

The example of FIG. 7, like FIGS. 1, 2, 3 and 4, shows the distribution of the heat from the optional combined heat and power system used to produce mechanical and electrical energy to drive the mechanical vapor compression in stage 5 and stage 7, wherein the thermal energy of distillation and evaporation is greatly reduced and the electrical energy generated may be less than or equal to the amount needed to drive the compressor of the vapor compression system, leaving little or no residual electrical energy to serve the electrical demand of the other stages which require mechanical energy such as pumping, stirring as in the cooking in stage 2, and fermentation in stage 4. FIG. 7 shows the distillation in stage 5 by compression passes the latent heat on to a multi-effect evaporation in stage 7 for the concentration of the thin stillage bottoms from stage 5, and the cascaded steam from reboiler-evaporator together with the final evaporation effect is part of the mechanical vapor compression that recycles the steam back to drive the distillation stage 5. The waste heat from the optional combined heat and power is distributed to meet the thermal demands of a cook process stage 2, distillation stage 5, drying stage 7 with generated steam from the recovered heat from exhaust gases through vapor compression, and dehydration stage 8.

The example of FIG. 8, like FIGS. 1, 2, 3, and 4 shows the distribution of the heat from the optional combined heat and power system used to produce mechanical and electrical energy to drive the mechanical vapor compression in stage 5 and stage 7, wherein the thermal energy of distillation and evaporation is greatly reduced and the electrical energy generated may be less than or equal to the amount needed to drive the compressor of the vapor compression system, leaving little or no residual electrical energy to serve the electrical demand of the other stages which require mechanical energy such as pumping, stirring as in the cooking in stage 2, and fermentation in stage 4. FIG. 8 shows the distillation in stage 5 by compression passes the latent heat on to a multi-effect evaporation in stage 7 which is comprised of two separate reboilers, with the concentration of the thin stillage bottoms from the aqueous distillation tower of stage 5, and the cascaded steam from reboiler-evaporator together with the final evaporation effect is part of the mechanical vapor compression that recycles the steam back to drive the aqueous distillation tower of stage 5 and biochemical bottom product cascaded vapors from the organic reboiler to the organic distillation tower. The waste heat from the combined heat and power is distributed to meet the thermal demands of a cook process stage 2, and distillation stage 5.

The example of FIG. 9, like FIGS. 1, 2, 3, and 4 shows the distribution of the heat from the optional combined heat and power system used to produce mechanical and electrical energy to drive the mechanical vapor compression in stage 5, stage 7 and stage 8, wherein the thermal energy of distillation, evaporation, and dehydration is greatly reduced and the electrical energy generated may be less than or equal to the amount needed to drive the compressor of the vapor compression system, leaving little or no residual electrical energy to serve the electrical demand of the other stages which require mechanical energy such as pumping, stirring as in the cooking in stage 2, and fermentation in stage 4. The waste heat from the combined heat and power is distributed to meet the thermal demands of a cook process stage 2, distillation stage 5, and dehydration stage 8.

The example of FIG. 10, like FIGS. 1, 2, 3, 4, 5, 6, 7, 8, and 9, shows the capture of low-grade dryer exhaust heat from the stage 7 stillage handling and processing by passing it into a reboiler-evaporator where process water is boiled at low temperature. This low-pressure steam is raised in pressure and/or temperature, via mechanical vapor compression and/or thermal vapor compression, with the compressed steam being passed into the distillery as process steam. The dryer exhaust heat capture and conversion to compressed steam may be applied to any of the configurations of distillery or bio-refineries processes such as those shown in FIGS. 1, 2, 3, 4, 5, 6, 7, 8, 9 and 10.

In should be noted that regarding FIGS. 1 to 10, specific unit operations may be omitted in some embodiments, and in these or other embodiments, other unit operations not explicitly shown may be included. Additionally, multiple pieces of equipment, either in series or in parallel, may be utilized for any unit operations, pumps, etc. Also, solid, liquid, and gas streams produced or existing within the process may be independently recycled, passed to subsequent steps, or removed/purged from the process at any point.

As will be appreciated by a person of ordinary skill in the art, the principles of this disclosure may be applied to many biorefinery configurations beyond those explicitly disclosed or described in the drawings hereto. Various combinations are possible, and selected embodiments from some variations may be utilized or adapted to arrive at additional variations that do not necessarily include all features disclosed herein. In particular, while some embodiments are directed to ethanol as the primary biofuel/biochemical, the present invention is by no means limited to ethanol.

For example, the invention may be applied to ABE fermentation, producing a mixture of acetone, n-butanol, and ethanol. One or more additional distillation or other separation units may be included, to separate components of a fermentation mixture. Also, in some embodiments, the primary product is less volatile than water (at atmospheric pressure), rather than more volatile, as is the case with ethanol. An example of a biofuel/biochemical less volatile than water is isobutanol.

The present invention also provides a biofuel or biochemical product produced by a process comprising a method of modifying a distillery or biorefinery, wherein the distillery or biorefinery converts biomass into the biofuel or biochemical, and wherein the biofuel or biochemical is purified by distillation, the method comprising:
  (i) introducing a vapor compression unit comprising a mechanical vapor recompression (MVR) unit and/or thermal vapor recompression (TVR) unit to recover latent heat, evaporation, drying, and/or dehydration processes, and provide a reduction in process thermal energy usage in the distillery or biorefinery; and
  (ii) optionally introducing a combined heat and power (CHP) system having a CHP engine, to provide mechanical, electrical, and/or thermal energy for driving the vapor compression unit, wherein residual waste heat of the CHP engine offsets the process thermal energy usage in the distillery or biorefinery, in conjunction with the vapor compression unit; and wherein integration of the vapor compression unit with the optional CHP system is preferably balanced to optimize process energy requirements, process carbon intensity, and/or process energy costs.

These and other combinations of heat and power optimization are available by the mixed combination of mechanical vapor compression integrated together with combined heat and power. The integration of these two complementary technologies, wherein the vapor compression in distillation, evaporation, drying, and optionally dehydration reduces the total thermal energy demand of the distillery, and a portion of the saved thermal energy fuel is then dedicated to combined heat and power to offset process electrical energy, allows for a simultaneous reduction in the thermal energy demand and electrical energy demand, together with a reduction in process energy costs and reduced carbon intensity for the plant.

Some variations of the invention provide a method for optimizing energy usage, production economics, and environmental performance in modifying existing distillation systems. The operational capabilities of a distillation system are maintained while a more energy-efficient process is added that diverts some portion of the distilled vapors, which would otherwise be condensed, and compresses them, heating them and raising their boiling point. The compressed vapors are condensed in a reboiler, capturing the energy released that would otherwise be lost to cooling water flowing through a condenser. The method used to drive the compressor, the design of the reboiler, and generation of additional usable energy are balanced to provide fully redundant capabilities with respect to the existing system and the desired optimization.

In one aspect, a method is provided for the modification and augmentation of a distillery wherein the addition of the disclosed distillation methods for heat management by mechanical vapor compression which recovers the latent heat, provides a reduction in process thermal energy together with combined heat and power for the addition of mechanical and electrical energy for driving the compression, wherein the residual waste heat of the engine offsets thermal energy required in the distillery in conjunction with the vapor compression in distillation, evaporation, drying, and/or dehydration. The integration of the vapor compression with combined heat and power is balanced to optimize the reduction in process energy requirements, process carbon intensity and/or process energy costs.

In some embodiments, the vapor compression is sized or operated to reduce the thermal energy required in distillation, evaporation, drying, and/or dehydration in concert with the standard steam generator that is operated at a reduced rate as a result of the reduction in steam energy demand due to energy recovered by the mechanical vapor compression in distillation, evaporation, drying, and/or dehydration. In these or other embodiments, the optional combined heat and power system is sized or operated in concert with the mechanical or thermal demand of the vapor compression and the thermal energy demand of the distillery wherein part of, some of, or all of the thermal energy is provided by the waste heat recovered by the combined heat and power system.

The combination of mechanical vapor compression in distillation, evaporation, drying, and/or dehydration and combined heat and power allows balancing of use in the distillery based on the market price of process fuel energy and electrical energy unit price, wherein the total process energy is not minimized, though the process energy costs are minimized based on the relative pricing of the two energy sources.

Also, the combination of vapor compression in distillation, evaporation, drying, and/or dehydration and combined heat and power allows minimization of the carbon intensity of the process through selective usage of electricity and thermal fuel in a manner that minimizes the total carbon intensity of the process energy, though the process energy costs are not minimized because of the relative pricing of the two energy sources and the individual carbon intensities allocated to the thermal and electrical process energy lifecycles.

By recapturing and recycling process heat, the disclosed technology provides an option for expanding biofuels/biochemical production that:

(a) reduces or eliminates the need for additional steam-generating capacity;
(b) reduces or eliminates the need for additional cooling capacity; and
(c) reduces or eliminates seasonal production restrictions due to cooling system capacity limitations during high ambient temperatures and humidity.

In addition, the disclosed technology can permit production increases without exceeding allowable air emissions and water usage and discharge restrictions under existing environmental permits.

Some embodiments of the invention provide a system or sub-system comprising or consisting of the process or apparatus configuration depicted in any one of FIGS. 1 to 10, or portions thereof, or any other disclosure set forth herein. Some embodiments of the invention provide instructions to retrofit an existing distillery or biorefinery with the process or apparatus configuration depicted in any one of FIGS. 1 to 10, or portions thereof, or any other disclosure set forth herein.

The throughput, or process capacity, may vary widely from small laboratory-scale units to full commercial-scale biorefineries, including any pilot, demonstration, or semi-commercial scale. In various embodiments, the process capacity is at least about 1 kg/day, 10 kg/day, 100 kg/day, 1 ton/day (all tons are metric tons), 10 tons/day, 100 tons/day, 500 tons/day, 1000 tons/day, 2000 tons/day, 3000 tons/day, 4000 tons/day, or higher.

All publications, patents, and patent applications cited in this specification are incorporated herein by reference in their entirety as if each publication, patent, or patent application was specifically and individually put forth herein.

In this detailed description, reference has been made to multiple embodiments of the invention and non-limiting examples and drawings relating to how the invention can be understood and practiced. Other embodiments that do not provide all of the features and advantages set forth herein may be utilized, without departing from the spirit and scope of the present invention. This invention incorporates routine experimentation and optimization of the methods and systems described herein. Such modifications and variations are considered to be within the scope of the invention defined by the claims.

Where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially.

Therefore, to the extent that there are variations of the invention, which are within the spirit of the disclosure or equivalent to the inventions found in the appended claims, it is the intent that this patent will cover those variations as well. The present invention shall only be limited by what is claimed.

REFERENCES

U.S. Pat. No. 4,340,446 to Crawford, "Heat recovery in distillation process" (1982)

U.S. Pat. No. 4,422,903 to Messick et al., "Anhydrous ethanol distillation method and apparatus" (1983)

U.S. Pat. No. 4,539,076 to Swain, "Vapor compression distillation system" (1985)

U.S. Pat. No. 4,645,569 to Akabane, et al., "Process for producing anhydrous ethanol" (1987)

U.S. Pat. No. 4,692,218 to Houben et al., "Process for producing ethanol" (1987)

U.S. Pat. No. 4,746,610 to Wills et al., "Efficient use of thermal energy from an internal combustion engine in ethanol production" (1988)

U.S. Pat. No. 5,294,304 to Kano et al., "Process for the recovery of absolute ethanol by vapor compression extractive distillation" (1994)

U.S. Pat. No. 7,257,945 to Kass et al., "Stripping ethanol from ethanol-blended fuels for use in $NO_x$ SCR" (2007)

U.S. Pat. No. 8,101,217 to Sovereign et al., "Method for ethanol production and extraction" (2012)

U.S. Pat. No. 8,101,808 to Evanko et al., "Recovery of higher alcohols from dilute aqueous solutions" (2012)

U.S. Pat. No. 8,114,255 to Vane et al., "Membrane-augmented distillation with compression to separate solvents from water" (2012)

U.S. Pat. No. 8,128,787 to Wynn et al., "Membrane-augmented distillation with pressure change to separate solvents from water" (2012)

U.S. Pat. No. 8,283,505 to Evanko et al., "Recovery of higher alcohols from dilute aqueous solutions" (2012)

U.S. Pat. No. 8,304,588 to Evanko et al., "Recovery of higher alcohols from dilute aqueous solutions" (2012)

U.S. Pat. No. 8,535,413 to Bryan et al., "Integrated mechanical vapor recompression (MVR) and membrane vapor permeation process for ethanol recovery (ethanol dehydration) from fermentation broth" (2013)

U.S. Pat. No. 8,614,077 to Evanko et al., "Recovery of higher alcohols from dilute aqueous solutions" (2013)

U.S. Pat. No. 9,138,678 to Huang et al., "Membrane-augmented distillation with compression and condensation to separate solvents from water" (2015)

U.S. Pat. No. 5,772,850 to Bobby D. Morris "Apparatus for vapor compression distillation" (1998)

U.S. Pat. No. 4,536,258 Esko Huhta-Koivisto "Distilling apparatus operating on the thermocompressor principle" (1985)

U.S. Pat. No. 4,585,523 Edward H. Giddings "Vapor compression distillation apparatus" (1984)

What is claimed is:

1. A distillery or biorefinery, wherein said distillery or biorefinery is capable of converting biomass into a biofuel or biochemical, said distillery or biorefinery comprising:
   (i) a biomass-conversion sub-system configured to convert said biomass into sugars;
   (ii) a fermentation sub-system configured to ferment said sugars into said biofuel or biochemical;
   (iii) a distillation sub-system configured to purify said biofuel or biochemical via distillation and to generate stillage, wherein said distillation sub-system includes one or more distillation units;
   (iv) at least one separation sub-system configured to further process said biofuel or biochemical and/or to further process said stillage;
   (v) a vapor compression sub-system comprising a mechanical vapor recompression (MVR) unit and/or a thermal vapor recompression (TVR) unit, wherein said vapor compression sub-system is configured to compress distillation vapors exiting said one or more distillation units, thereby providing compressed distillation vapors with an increased boiling point and preserving latent heat of said compressed distillation vapors from said one or more distillation units, wherein said latent heat from said distillation sub-system is integrated with at least one distinct distillery or biorefinery process unit that (a) is not configured for distillation, (b) is not part of said distillation sub-system, (c) is not part of said vapor compression sub-system, and (d) generates a distinctly different vapor stream than said compressed distillation vapors, wherein said compressed distillation vapors are condensed to cascade said latent heat of said compressed distillation vapors to said distinct distillery or biorefinery process unit and provide a reduction in process thermal energy usage in said distillery or biorefinery; and
   (vi) a source of power configured to provide mechanical, electrical, and/or thermal energy for driving said vapor compression sub-system.

2. The distillery or biorefinery of claim 1, wherein said vapor compression sub-system comprises multiple mechanical and/or thermal compressors or vapor jets, wherein cascaded heat to or from said distillation sub-system is integrated with multiple evaporations of said stillage and/or dehydration and/or drying, and wherein compressed biofuel or biochemical vapors and generated steam are returned to said distillation sub-system within said distillery or biorefinery.

3. The distillery or biorefinery of claim 1, wherein said vapor compression sub-system comprises multiple mechanical and/or thermal compressors or vapor jets, wherein cascaded heat to or from said distillation sub-system is integrated with multiple evaporations of said stillage including a first or last multiple evaporator, wherein compressed steam from said first evaporator is optionally split between said distillation sub-system and a part of said multiple stillage evaporations, and wherein a compressor stage is configured to cascade heat of evaporation between said distillation sub-system and said multiple stillage evaporations.

4. The distillery or biorefinery of claim 1, wherein said vapor compression sub-system comprises multiple mechanical and/or thermal compressors or vapor jets, wherein cascaded heat to or from multiple evaporations of said stillage to said distillation sub-system is integrated with compression of steam to or from at least one reboiler-evaporator to drive said distillation and partial evaporation, and/or wherein compressor stages are configured to cascade latent heat into an evaporation unit.

5. The distillery or biorefinery of claim 1, wherein said vapor compression sub-system comprises multiple mechanical and/or thermal compressors or vapor jets, and wherein cascaded heat from said distillation sub-system is integrated to drive vapor-phase dehydration of a vapor stream output of said distillation sub-system.

6. The distillery or biorefinery of claim 1, wherein said distillery or biorefinery comprises a dryer configured for drying said stillage, and wherein said vapor compression sub-system comprises both an MVR unit configured to recover heat of said distillation and a TVR unit configured to recover heat from exhaust gases from said dryer.

7. The distillery or biorefinery of claim 1, wherein said distillery or biorefinery comprises a dryer configured for drying said stillage, wherein said vapor compression sub-system comprises multiple mechanical and/or thermal compressors or vapor jets, and wherein cascaded heat from an exhaust of said dryer, recaptured by a reboiler-evaporator, is integrated to provide steam for other plant units.

8. The distillery or biorefinery of claim 1, wherein said source of power is a combined heat and power (CHP) sub-system having a CHP engine, and wherein said CHP sub-system and said vapor compression sub-system are integrated and configured so that residual waste heat of said CHP engine offsets process thermal energy usage in said distillery or biorefinery.

9. The distillery or biorefinery of claim 8, wherein said CHP engine is sized in concert with energy demand of said vapor compression sub-system and/or thermal energy demand of said distillery or biorefinery, and wherein waste heat recovered by said CHP sub-system provides at least some of said thermal energy demand of said distillery or biorefinery.

10. The distillery or biorefinery of claim 8, wherein said vapor compression sub-system comprises a TVR unit, and wherein said CHP engine is sized in concert with motive vapor demand of said TVR unit.

11. A method of integration in a distillery or biorefinery, wherein said distillery or biorefinery converts biomass into a biofuel or biochemical, said method comprising:
(i) providing said biomass and converting said biomass into sugars;
(ii) fermenting said sugars into said biofuel or biochemical;
(iii) purifying said biofuel or biochemical in one or more distillation units, wherein stillage is generated;
(iv) in one or more separation units, further processing said biofuel or biochemical and/or further processing said stillage;
(v) introducing a vapor compression unit comprising a mechanical vapor recompression (MVR) unit and/or a thermal vapor recompression (TVR) unit to compress distillation vapors exiting said one or more distillation units, thereby providing compressed distillation vapors with an increased boiling point and preserving latent heat of said compressed distillation vapors from said one or more distillation units, wherein said latent heat from said one or more distillation units is integrated with at least one distinct distillery or biorefinery process step that (a) is not a distillation step and (b) generates a distinctly different vapor stream than said compressed distillation vapors, wherein said compressed distillation vapors are condensed to cascade said latent heat of said compressed distillation vapors to said distinct distillery or biorefinery process step and provide a reduction in process thermal energy usage in said distillery or biorefinery; and
(vi) introducing a source of power to provide mechanical, electrical, and/or thermal energy for driving said vapor compression unit.

12. The method of claim 11, wherein said vapor compression unit comprises multiple mechanical and/or thermal vapor compressors or vapor jets, wherein cascaded heat from said one or more distillation units is integrated with multiple stillage evaporations and/or dehydration and/or drying, and wherein compressed biofuel or biochemical vapors and generated steam are returned to said one or more distillation units.

13. The method of claim 11, wherein said vapor compression unit comprises multiple mechanical and/or thermal vapor compressors or vapor jets, wherein cascaded heat from said one or more distillation units is integrated with multiple evaporations of said stillage including a first evaporator, wherein compressed steam from said first evaporator is optionally split between said one or more distillation units and a part of said multiple stillage evaporations, and wherein said one or more distillation units and at least a portion of said multiple evaporations of said stillage are operated at equal or near-equal pressure, thereby allowing a compressor stage to cascade heat of evaporation between said one or more distillation units and said multiple evaporations of said stillage and optionally vapor-phase dehydration.

14. The method of claim 11, wherein said vapor compression unit comprises multiple mechanical and/or thermal vapor compressors or vapor jets, wherein cascaded heat from multiple evaporations of said stillage to said one or more distillation units is integrated with compression of steam from at least one reboiler-evaporator to drive distillation and partial evaporation, and wherein said distillation and said partial evaporation are operated such that evaporation pressure is higher than distillation pressure, thereby allowing compressor stages to cascade the heat of evaporation into said one or more distillation units.

15. The method of claim 14, wherein compression of distillation vapors is integrated with dehydration of distillation vapors at a sufficient pressure to generate a final product containing said biofuel or biochemical.

16. The method of claim 11, wherein said vapor compression unit is sized or operated with a standard steam generator for reduction of thermal energy required in steps (iii) and/or (iv), and wherein said standard steam generator is operated at a reduced rate as a result of reduction in steam energy demand due to energy recovered by said vapor compression unit.

17. The method of claim 11, wherein said source of power is a combined heat and power (CHP) system having a CHP engine, wherein residual waste heat of said CHP engine offsets process thermal energy usage in said distillery or biorefinery in conjunction with said vapor compression unit, wherein integration of said vapor compression unit with said CHP system is balanced to optimize process energy requirements, process carbon intensity, and/or process energy costs.

18. The method of claim 17, wherein said vapor compression unit comprises a TVR unit, and wherein said CHP engine is sized or operated in concert with thermal energy demand for producing steam or biochemical motive vapors to drive said TVR unit.

19. The method of claim 17, wherein integration of said vapor compression unit with said CHP system allows balancing of use in said distillery or biorefinery of process fuel energy, electrical energy unit price, and process carbon intensity, wherein said process energy costs are minimized based on relative market pricing of said process fuel energy and said electrical energy, and optionally wherein total process energy is not minimized.

20. The method of claim 11, wherein said biofuel or biochemical is selected from the group consisting of methanol, ethanol, 1-propanol, 2-propanol, n-butanol, isobutanol, 2-butanol, tert-butanol, acetone, and combinations thereof.

21. The distillery or biorefinery of claim 1, wherein said latent heat from said distillation unit is integrated with at least one distillery or biorefinery process unit contained within said biomass-conversion sub-system, said fermentation sub-system, or said separation sub-system.

22. The method of claim 11, wherein said latent heat from said one or more distillation units is integrated with at least one step selected from steps (i), (ii), or (iv).

* * * * *